United States Patent
Huber et al.

(10) Patent No.: US 8,522,312 B2
(45) Date of Patent: Aug. 27, 2013

(54) ACCESS CONTROL LISTS AND PROFILES TO MANAGE FEMTO CELL COVERAGE

(75) Inventors: Kurt Donald Huber, Kennesaw, GA (US); Judson John Flynn, Decatur, GA (US); William Gordon Mansfield, Sugar Hill, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 535 days.

(21) Appl. No.: 12/276,058

(22) Filed: Nov. 21, 2008

(65) Prior Publication Data

US 2009/0288140 A1 Nov. 19, 2009

Related U.S. Application Data

(60) Provisional application No. 61/052,813, filed on May 13, 2008.

(51) Int. Cl.
*G06F 21/00* (2006.01)

(52) U.S. Cl.
USPC .............................................. 726/3

(58) Field of Classification Search
USPC .................................. 726/3, 4, 17
See application file for complete search history.

(56) References Cited

U.S. PATENT DOCUMENTS

| | | | |
|---|---|---|---|
| 5,745,559 A | 4/1998 | Weir | |
| 5,864,764 A | 1/1999 | Thro et al. | |
| 6,052,594 A | 4/2000 | Chuang et al. | |
| 6,151,505 A | 11/2000 | Larkins | |
| 6,208,659 B1 | 3/2001 | Govindarajan et al. | |
| 6,219,786 B1 | 4/2001 | Cunningham et al. | |
| 6,256,504 B1 | 7/2001 | Tell et al. | |
| 6,266,537 B1 | 7/2001 | Kashitani et al. | |
| 6,363,261 B1 | 3/2002 | Raghavan | |
| 6,483,852 B1 | 11/2002 | Jacquet et al. | |
| 6,484,096 B2 | 11/2002 | Wong | |

(Continued)

FOREIGN PATENT DOCUMENTS

| | | |
|---|---|---|
| CN | 101017554 A | 8/2007 |
| CN | 101175333 A | 5/2008 |

(Continued)

OTHER PUBLICATIONS

OA dated Jun. 17, 2010 for U.S. Appl. No. 11/457,129, 15 pages.

(Continued)

*Primary Examiner* — Brandon Hoffman
*Assistant Examiner* — Anthony Brown
(74) *Attorney, Agent, or Firm* — Turocy & Watson, LLP

(57) ABSTRACT

System(s) and method(s) provide access management to femto cell service through access control list(s) (e.g., white list(s), or black list(s)). White list(s) includes a set of subscriber station(s) identifier numbers, codes, or tokens, and also can include additional fields for femto cell access management based on desired complexity. White list(s) can have associated white list profile(s) therewith to establish logic of femto coverage access based on the white list(s). Values of attribute fields that determine white list(s), black list(s), or white list profile(s) can be generated through various sources. An access list management component facilitates generation and maintenance of white list(s), black list(s), or white list profile(s). Values for identifier attribute field(s) available for inclusion in a white list are validated prior to inclusion therein. Various example aspects such as white list(s) management, maintenance and dissemination; automatic population or pre-configuration; and inclusion of wireless device(s) or subscriber(s) are also provided.

32 Claims, 22 Drawing Sheets

(56) References Cited

U.S. PATENT DOCUMENTS

| | | |
|---|---|---|
| 6,512,478 B1 | 1/2003 | Chien |
| 6,710,651 B2 | 3/2004 | Forrester |
| 6,718,023 B1 | 4/2004 | Zolotov |
| 7,080,139 B1 | 7/2006 | Briggs et al. |
| 7,142,861 B2 | 11/2006 | Murai |
| 7,146,153 B2 | 12/2006 | Russell |
| 7,209,739 B1 | 4/2007 | Narayanabhatla |
| 7,277,410 B2 | 10/2007 | Horneman |
| 7,317,931 B2 | 1/2008 | Guo |
| 7,370,356 B1 | 5/2008 | Guo |
| 7,437,755 B2 | 10/2008 | Farino et al. |
| 7,493,390 B2 | 2/2009 | Bobde et al. |
| 7,496,383 B2 | 2/2009 | Kurata |
| 7,516,219 B2 | 4/2009 | Moghaddam et al. |
| 7,613,444 B2 | 11/2009 | Lindqvist et al. |
| 7,614,078 B1 | 11/2009 | Stieglitz et al. |
| 7,623,857 B1 | 11/2009 | O'Neil |
| 7,633,910 B2 | 12/2009 | Zhun et al. |
| 7,751,826 B2 | 7/2010 | Gardner |
| 7,761,526 B2 | 7/2010 | Pounds et al. |
| 7,768,983 B2 | 8/2010 | Nylander et al. |
| 7,853,265 B1 | 12/2010 | Ahmad et al. |
| 7,885,644 B2 | 2/2011 | Gallagher et al. |
| 7,929,537 B2 | 4/2011 | Vasudevan et al. |
| 7,929,970 B1* | 4/2011 | Gunasekara et al. ......... 455/444 |
| 7,941,144 B2 | 5/2011 | Nylander et al. |
| 7,995,994 B2 | 8/2011 | Khetawat et al. |
| 8,064,909 B2 | 11/2011 | Spinelli et al. |
| 8,108,923 B1 | 1/2012 | Satish et al. |
| 2002/0098837 A1 | 7/2002 | Ferrario et al. |
| 2002/0123365 A1 | 9/2002 | Thorson |
| 2002/0142791 A1 | 10/2002 | Chen et al. |
| 2003/0028621 A1 | 2/2003 | Furlong et al. |
| 2003/0109271 A1 | 6/2003 | Lewis et al. |
| 2003/0125044 A1 | 7/2003 | Deloach |
| 2003/0139180 A1 | 7/2003 | McIntosh et al. |
| 2003/0142637 A1 | 7/2003 | Khawer et al. |
| 2003/0144793 A1 | 7/2003 | Melaku et al. |
| 2003/0153302 A1* | 8/2003 | Lewis et al. .................... 455/412 |
| 2004/0111382 A1 | 6/2004 | Haji-Ioannou |
| 2004/0125781 A1 | 7/2004 | Walter et al. |
| 2004/0203846 A1 | 10/2004 | Caronni et al. |
| 2004/0236702 A1 | 11/2004 | Fink et al. |
| 2004/0258003 A1 | 12/2004 | Kotot et al. |
| 2005/0003797 A1 | 1/2005 | Baldwin |
| 2005/0009499 A1 | 1/2005 | Koster |
| 2005/0026650 A1 | 2/2005 | Russell |
| 2005/0075114 A1 | 4/2005 | Dennison et al. |
| 2005/0108529 A1 | 5/2005 | Juneau |
| 2005/0144279 A1 | 6/2005 | Wexelblat |
| 2005/0160276 A1 | 7/2005 | Braun et al. |
| 2005/0172148 A1 | 8/2005 | Ying |
| 2005/0177645 A1 | 8/2005 | Dowling et al. |
| 2005/0223389 A1 | 10/2005 | Klein et al. |
| 2005/0250527 A1 | 11/2005 | Jugl |
| 2005/0254451 A1 | 11/2005 | Grosbach |
| 2005/0269402 A1 | 12/2005 | Spitzer et al. |
| 2006/0031387 A1 | 2/2006 | Hamzeh et al. |
| 2006/0031493 A1 | 2/2006 | Cugi |
| 2006/0046647 A1 | 3/2006 | Parikh et al. |
| 2006/0074814 A1 | 4/2006 | Lovell et al. |
| 2006/0075098 A1 | 4/2006 | Becker et al. |
| 2006/0182074 A1 | 8/2006 | Kubler et al. |
| 2006/0223498 A1 | 10/2006 | Gallagher et al. |
| 2006/0281457 A1 | 12/2006 | Huotari et al. |
| 2007/0002844 A1 | 1/2007 | Ali |
| 2007/0008894 A1 | 1/2007 | Lynch et al. |
| 2007/0025245 A1 | 2/2007 | Porras et al. |
| 2007/0032225 A1 | 2/2007 | Konicek et al. |
| 2007/0032269 A1 | 2/2007 | Shostak |
| 2007/0074272 A1 | 3/2007 | Watanabe |
| 2007/0094601 A1 | 4/2007 | Greenberg et al. |
| 2007/0097093 A1 | 5/2007 | Ohshita et al. |
| 2007/0097938 A1 | 5/2007 | Nylander et al. |
| 2007/0097939 A1 | 5/2007 | Nylander et al. |
| 2007/0097983 A1 | 5/2007 | Nylander et al. |
| 2007/0099561 A1 | 5/2007 | Voss |
| 2007/0111706 A1 | 5/2007 | Kumar et al. |
| 2007/0123253 A1 | 5/2007 | Simongini et al. |
| 2007/0124802 A1 | 5/2007 | Anton et al. |
| 2007/0133563 A1 | 6/2007 | Hundscheidt et al. |
| 2007/0155421 A1 | 7/2007 | Alberth et al. |
| 2007/0167175 A1 | 7/2007 | Wong |
| 2007/0183427 A1 | 8/2007 | Nylander et al. |
| 2007/0184815 A1 | 8/2007 | Aebi |
| 2007/0199076 A1 | 8/2007 | Rensin et al. |
| 2007/0220252 A1 | 9/2007 | Sinko et al. |
| 2007/0232332 A1 | 10/2007 | Holur et al. |
| 2007/0258418 A1 | 11/2007 | Wurtenberger et al. |
| 2007/0270152 A1 | 11/2007 | Nylander et al. |
| 2007/0275739 A1 | 11/2007 | Blackburn |
| 2007/0287501 A1 | 12/2007 | Hoshina |
| 2008/0043972 A1 | 2/2008 | Ruetschi et al. |
| 2008/0049702 A1 | 2/2008 | Meylan et al. |
| 2008/0065752 A1 | 3/2008 | Ch'ng et al. |
| 2008/0076392 A1 | 3/2008 | Khetawat et al. |
| 2008/0076393 A1 | 3/2008 | Khetawat et al. |
| 2008/0076398 A1 | 3/2008 | Mate et al. |
| 2008/0076412 A1 | 3/2008 | Khetawat et al. |
| 2008/0076419 A1 | 3/2008 | Khetawat et al. |
| 2008/0076420 A1 | 3/2008 | Khetawat et al. |
| 2008/0076425 A1 | 3/2008 | Khetawat et al. |
| 2008/0081636 A1* | 4/2008 | Nylander et al. ......... 455/452.2 |
| 2008/0082538 A1 | 4/2008 | Meijer et al. |
| 2008/0119160 A1 | 5/2008 | Andriantsiferana et al. |
| 2008/0126531 A1 | 5/2008 | Setia et al. |
| 2008/0132239 A1 | 6/2008 | Khetawat et al. |
| 2008/0133742 A1 | 6/2008 | Southiere et al. |
| 2008/0151807 A1 | 6/2008 | Meier et al. |
| 2008/0168099 A1 | 7/2008 | Skaf |
| 2008/0181184 A1 | 7/2008 | Kezys |
| 2008/0201076 A1 | 8/2008 | Huang et al. |
| 2008/0207170 A1 | 8/2008 | Khetawat et al. |
| 2008/0242280 A1 | 10/2008 | Shapiro et al. |
| 2008/0244148 A1 | 10/2008 | Nix et al. |
| 2008/0254792 A1 | 10/2008 | Ch'ng |
| 2008/0261602 A1 | 10/2008 | Livneh |
| 2008/0281687 A1 | 11/2008 | Hurwitz et al. |
| 2008/0282327 A1 | 11/2008 | Winget et al. |
| 2008/0299984 A1 | 12/2008 | Shimomura |
| 2008/0299992 A1 | 12/2008 | Eitan et al. |
| 2008/0305792 A1 | 12/2008 | Khetawat et al. |
| 2008/0305801 A1 | 12/2008 | Burgess et al. |
| 2008/0305834 A1 | 12/2008 | Janiszewski et al. |
| 2008/0318551 A1 | 12/2008 | Palamara et al. |
| 2009/0012898 A1 | 1/2009 | Sharma et al. |
| 2009/0031006 A1 | 1/2009 | Johnson et al. |
| 2009/0037973 A1 | 2/2009 | Gustave et al. |
| 2009/0042593 A1 | 2/2009 | Yavuz et al. |
| 2009/0046665 A1 | 2/2009 | Robson et al. |
| 2009/0047945 A1 | 2/2009 | Zhang |
| 2009/0059822 A1 | 3/2009 | Morrill et al. |
| 2009/0061821 A1 | 3/2009 | Chen et al. |
| 2009/0061873 A1 | 3/2009 | Bao et al. |
| 2009/0082010 A1 | 3/2009 | Lee |
| 2009/0082020 A1* | 3/2009 | Ch'ng et al. ............... 455/435.3 |
| 2009/0092096 A1 | 4/2009 | Czaja |
| 2009/0092097 A1 | 4/2009 | Nylander et al. |
| 2009/0093232 A1 | 4/2009 | Gupta et al. |
| 2009/0094351 A1 | 4/2009 | Gupta et al. |
| 2009/0094680 A1 | 4/2009 | Gupta et al. |
| 2009/0097436 A1 | 4/2009 | Vasudevan et al. |
| 2009/0111499 A1 | 4/2009 | Bosch |
| 2009/0122773 A1 | 5/2009 | Gogic |
| 2009/0124262 A1 | 5/2009 | Vela et al. |
| 2009/0129336 A1 | 5/2009 | Osborn et al. |
| 2009/0129350 A1 | 5/2009 | Khandekar et al. |
| 2009/0131050 A1 | 5/2009 | Osborn |
| 2009/0131098 A1 | 5/2009 | Khandekar et al. |
| 2009/0135749 A1 | 5/2009 | Yang |
| 2009/0135794 A1 | 5/2009 | Su et al. |
| 2009/0156213 A1 | 6/2009 | Spinelli et al. |
| 2009/0163216 A1* | 6/2009 | Hoang et al. ................... 455/450 |
| 2009/0163224 A1 | 6/2009 | Dean |

| | | | |
|---|---|---|---|
| 2009/0170440 | A1 | 7/2009 | Eyuboglu et al. |
| 2009/0170528 | A1 | 7/2009 | Bull et al. |
| 2009/0180428 | A1 | 7/2009 | Viswanath |
| 2009/0191844 | A1* | 7/2009 | Morgan et al. ............... 455/411 |
| 2009/0191845 | A1 | 7/2009 | Morgan et al. |
| 2009/0210324 | A1 | 8/2009 | Bhogal |
| 2009/0213825 | A1 | 8/2009 | Gupta et al. |
| 2009/0215429 | A1 | 8/2009 | Caldwell et al. |
| 2009/0215452 | A1 | 8/2009 | Balasubramanian et al. |
| 2009/0221303 | A1 | 9/2009 | Soliman |
| 2009/0233574 | A1 | 9/2009 | Shinozaki |
| 2009/0245176 | A1 | 10/2009 | Balasubramanian et al. |
| 2009/0253421 | A1 | 10/2009 | Camp et al. |
| 2009/0253432 | A1 | 10/2009 | Willey et al. |
| 2009/0279701 | A1 | 11/2009 | Moisand et al. |
| 2009/0291667 | A1 | 11/2009 | Vakil et al. |
| 2009/0325634 | A1 | 12/2009 | Bienas et al. |
| 2010/0022266 | A1 | 1/2010 | Villier |
| 2010/0040026 | A1 | 2/2010 | Melkesetian |
| 2010/0048165 | A1 | 2/2010 | Caldwell et al. |
| 2010/0113067 | A1 | 5/2010 | Fullam et al. |
| 2010/0260068 | A1 | 10/2010 | Bhatt et al. |
| 2011/0177794 | A1 | 7/2011 | Nylander et al. |
| 2011/0200022 | A1 | 8/2011 | Annamalai |
| 2011/0280154 | A1 | 11/2011 | Silverstrim et al. |

FOREIGN PATENT DOCUMENTS

| | | |
|---|---|---|
| GB | 2425291 A | 10/2006 |
| GB | 2425921 A | 11/2006 |
| JP | 2003288521 | 10/2003 |
| JP | 2005073147 | 3/2005 |
| JP | 2006067143 | 3/2006 |
| JP | 2008048055 | 2/2008 |
| WO | 2005076964 A2 | 8/2005 |
| WO | 2007015067 A2 | 2/2007 |
| WO | 2007040449 A1 | 4/2007 |
| WO | 2008047039 A1 | 4/2008 |

OTHER PUBLICATIONS

Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
International Search Report and Written Opinion dated Oct. 27, 2009 for PCT Application Serial No. PCT/US2009/043861, 14 Pages.
International Search Report and Written Opinion mailed Feb. 23, 2010, for PCT Application No. PCT/US2009/043846, 13 pages.
OA dated Dec. 31, 2009 for U.S. Appl. No. 11/457,129, 16 pages.
OA dated Apr. 17, 2009 for U.S. Appl. No. 11/276,269, 15 pages.
OA dated Nov. 4, 2008 for U.S. Appl. No. 11/276,269, 15 pages.
OA dated Jun. 14, 2011 for U.S. Appl. No. 12/275,878, 35 pages.
OA dated Jun. 22, 2011 for U.S. Appl. No. 12/484,072, 38 pages.
OA dated Jul. 7, 2011 for U.S. Appl. No. 12/276,257, 24 pages.
OA dated Jun. 28, 2011 for U.S. Appl. No. 12/275,925, 18 pages.
OA dated Jun. 8, 2011 for U.S. Appl. No. 12/484,026, 30 pages.
OA dated Mar. 29, 2011 for U.S. Appl. No. 12/276,002, 37 pages.
OA dated Apr. 19, 2011 for U.S. Appl. No. 12/276,238, 22 pages.
OA dated May 5, 2011 for U.S. Appl. No. 12/275,015, 32 pages.
OA dated Oct. 24, 2011 for U.S. Appl. No. 12/275,925, 14 pages.
OA dated Nov. 30, 2011 for U.S. Appl. No. 12/275,878, 38 pages.
OA dated Dec. 1, 2011 for U.S. Appl. No. 12/275,996, 44 pages.
OA dated Oct. 25, 2011 for U.S. Appl. No. 12/465,580, 39 pages.
OA dated Nov. 8, 2011 for U.S. Appl. No. 12/465,468, 50 pages.
OA dated Jan. 5, 2012 for U.S. Appl. No. 12/465,585, 43 pages.
OA dated Dec. 28, 2011 for U.S. Appl. No. 12/175,293, 38 pages.
OA dated Nov. 21, 2011 for U.S. Appl. No. 12/484,026, 37 pages.
OA dated Dec. 14, 2011 for U.S. Appl. No. 12/484,072, 44 pages.
OA dated Nov. 1, 2011 for U.S. Appl. No. 12/816,087, 33 pages.
OA dated Mar. 5, 2012 for U.S. Appl. No. 12/465,598, 55 pages.
OA dated Mar. 19, 2012 for U.S. Appl. No. 12/276,120, 68 pages.
OA dated Mar. 30, 2012 for U.S. Appl. No. 12/484,026, 30 pages.
Notice of Allowance dated Apr. 3, 2012 for U.S. Appl. No. 12/275,996, 38 pages.
OA dated Apr. 10, 2012 for U.S. Appl. No. 12/275,416, 32 pages.
OA dated Apr. 10, 2012 for U.S. Appl. No. 12/484,135, 45 pages.
OA dated Apr. 13, 2012 for U.S. Appl. No. 13/316,106, 35 pages.
Notice of Allowance dated Apr. 25, 2012 for U.S. Appl. No. 12/465,468, 35 pages.
OA dated May 8, 2012 for U.S. Appl. No. 11/457,129, 38 pages.
OA dated Jul. 16, 2012 for U.S. Appl. No. 12/275,878, 37 pages.
OA dated Jul. 10, 2012 for U.S. Appl. No. 12/465,585, 32 pages.
OA dated Sep. 5, 2012 for U.S. Appl. No. 12/276,120, 49 pages.
OA dated Aug. 16, 2012 for U.S. Appl. No. 12/465,598, 31 pages.
OA dated Sep. 6, 2012 for U.S. Appl. No. 12/579,957, 51 pages.
OA dated Sep. 10, 2012 for U.S. Appl. No. 12/276,002, 54 pages.
OA dated Aug. 18, 2011 for U.S. Appl. No. 12/275,416, 39 pages.
OA dated Sep. 14, 2011 for U.S. Appl. No. 12/276,002, 35 pages.
OA dated Oct. 6, 2011 for U.S. Appl. No. 12/465,483, 50 pages.
OA dated Oct. 4, 2011 for U.S. Appl. No. 12/484,135, 44 pages.
OA dated Jul. 21, 2011 for U.S. Appl. No. 12/175,293, 30 pages.
Office Action dated Jan. 17, 2013 for U.S. Appl. No. 13/554,710, 42 pages.
Final Office Action dated Feb. 15, 2013 for U.S. Appl. No. 12/579,957, 17 pages.
Office Action dated Feb. 26, 2013 for U.S. Appl. No. 12/276,120, 59 pages.
Chinese Office Action for Chinese Application No. 200980117263.8 dated Feb. 16, 2013, 7 pgs.
Chinese Office Action for Chinese Application No. 200980117188.5 dated Jan. 31, 2013, 11 pgs.
Final Office Action dated Mar. 14, 2013 for U.S. Appl. No. 12/484,072, 34 pages.
OA dated Oct. 2, 2012 for U.S. Appl. No. 12/484,026, 29 pages.
OA dated Oct. 11, 2012 for U.S. Appl. No. 13/487,794, 45 pages.
OA dated Oct. 9, 2012 for U.S. Appl. No. 13/298,924, 51 pages.
OA dated Nov. 5, 2012 for U.S. Appl. No. 12/484,072, 52 pages.
OA dated Nov. 20, 2012 for U.S. Appl. No. 12/275,878, 28 pages.
Japanese Office Action mailed Sep. 13, 2012 for Japanese Patent Application No. 2011-509669, 10 pages.
Canadian Office Action mailed Oct. 30, 2012 for Canadian Patent Application No. 2,722,324, 3 pages.
Japanese Office Action mailed Sep. 13, 2012 for Japanese Patent Application 2011-509675, 4 pages.
Office Action dated Dec. 3, 2012 for U.S. Appl. No. 12/275,416, 33 pages.
Office Action dated Apr. 23, 2013 for U.S. Appl. No. 12/175,293, 41 pages.
Canadian Office Action mailed Mar. 26, 2013 for Canadian Patent Application No. 2,722,324, 4 pages.
Office Action dated Jul. 15, 2013 for U.S. Appl. No. 13/554,710, 37 pages.

* cited by examiner

ACCESS CONTROL LISTS AND PROFILES TO MANAGE FEMTO CELL COVERAGE

CROSS-REFERENCE TO RELATED APPLICATION

This application claims the benefit of U.S. Provisional Patent application Ser. No. 61/052,813 entitled "MANAGEMENT OF ACCESS TO FEMTO CELL COVERAGE" and filed on May 13, 2008. The entirety of the above-referenced application is incorporated by reference herein.

TECHNICAL FIELD

The subject innovation relates to wireless communications and, more particularly, to management of access to femto cell coverage by a subscriber and subscriber stations.

BACKGROUND

Femto cells—building-based wireless access points interfaced with a wired broadband network—are generally deployed to improve indoor wireless coverage provided by a wireless network operator. Femto cells typically operate in licensed portions of the electromagnetic spectrum, and generally offer plug-and-play installation; e.g., automatic configuration of femto access point. Improved indoor coverage includes stronger signal and improved reception (e.g., voice or sound), ease of session or call initiation and session or call retention as well. Coverage of a femto cell, or femto AP, is intended to be confined within the bounds of an indoor compound, in order to mitigate interference among mobile stations covered by a macro cell and terminals covered by the femto AP. Additionally, confined coverage can reduce crosstalk among terminals serviced by disparate, neighboring femto cells as well.

Coverage improvements via femto cells can also mitigate customer attrition as long as a favorable subscriber perception regarding voice coverage and other data services with substantive delay sensitivity is attained. A positive customer experience can depend on adequate access management to femto cell service. Such adequate access management can include configuration procedures of a provisioned femto cell access point deployed in a coverage area. Thus, cumbersome configuration procedures that (i) involve interaction with customer service representatives; (ii) fail to provide versatility and autonomy, with substantially low complexity; or (iii) fail to be directed to a broad spectrum of consumers with various disparate degrees of technological savvy, can hinder femto cell service adoption and thus prevent pervasive dissemination of utilization of home-based and business-based femto access points and exploitation of operational efficiencies thereof.

SUMMARY

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The subject innovation provides system(s) and method(s) to manage access to femto cell service through access control list(s), e.g., white list(s) or black list(s). Such access control list(s) can be configured through various apparatuses and in various modes, e.g., intractively or automatically, which facilitates access management of access to femto cell coverage. White list(s) includes a set of subscriber station(s) identifier numbers, codes or tokens, and can also include additional fields that can contain information respectively associated with communication devices to facilitate femto cell access management based at least in part on desired complexity; for instance, an additional field in a white list can be a logic parameter that determines whether an associated identifier is available for dissemination across disparate white lists. Values of attribute fields that determine white list(s), black list(s), or white list profile(s) can be generated through various sources. An access list management component facilitates generation and maintenance of white list(s), black list(s), or white list profile(s). Values for identifier attribute field(s) available for inclusion in a white list are validated prior to inclusion therein. Various example aspects such as white list(s) management, maintenance and dissemination; automatic population or pre-configuration; and inclusion of wireless device(s) or subscriber(s) are also provided.

Various illustrative aspects such as white list(s) management, maintenance and dissemination; automatic population or pre-configuration; and inclusion of wireless device(s) or subscriber(s) are also provided.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention may be employed. Other aspects, advantages and novel features of the invention will become apparent from the following detailed description of the invention when considered in conjunction with the drawings.

DETAILED DESCRIPTION

Figure 1:
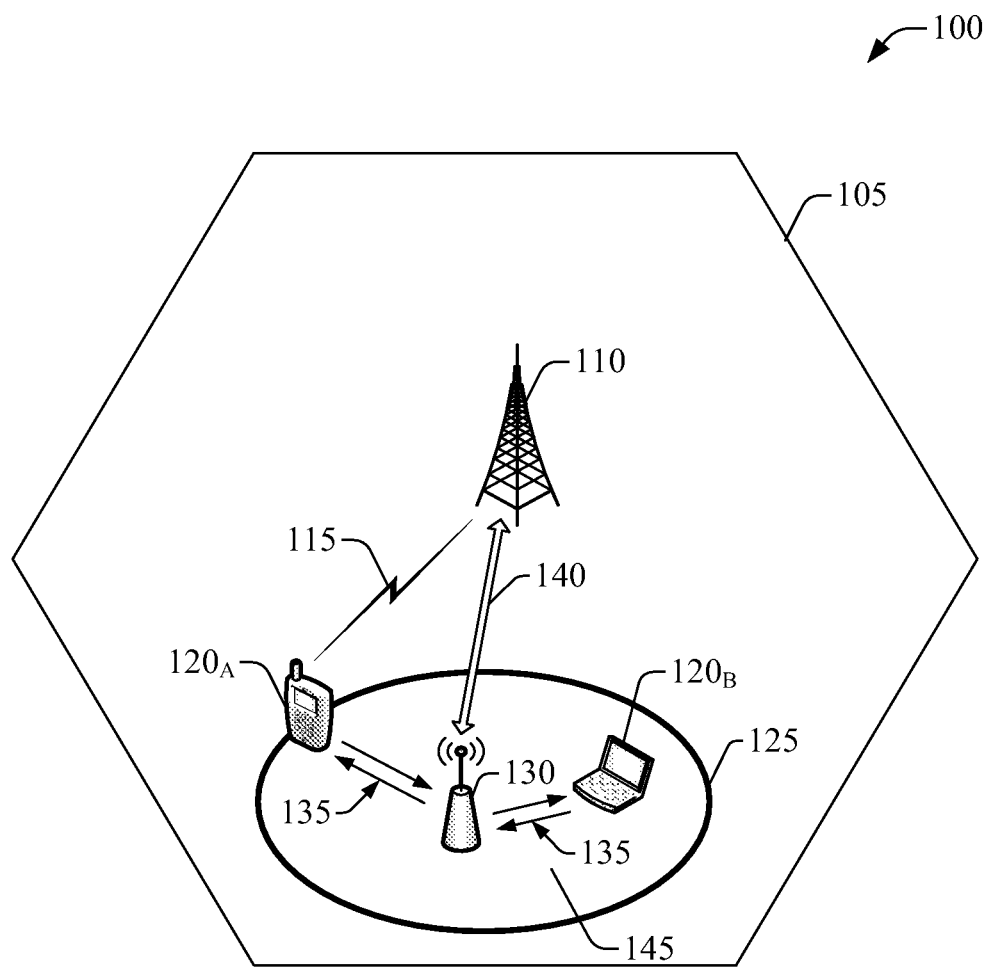
FIG. 1 a schematic deployment of a macro cell and a femto cell for wireless coverage in accordance with aspects described herein.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component," "system," "platform," and the like are intended to refer to a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," subscriber station," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B." "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows. Furthermore, the terms "access control list" and "access list" are also utilized interchangeably and intend to covey the same meaning unless otherwise explicitly noted.

Furthermore, the terms "user," "subscriber," "customer," "consumer," "prosumer," "agent," and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms) which can provide simulated vision, sound recognition and so forth. As utilized herein, the term "prosumer" indicate the following contractions: professional-consumer and producer-consumer.

Referring to the drawings, FIG. 1 illustrates a schematic wireless environment (e.g., a network) 100 in which a femto cell can exploits various aspects described in the subject specification. In wireless environment 100, area 105 represents a coverage macro cell which is served by base station 110. Macro coverage is generally intended for outdoors locations for servicing mobile wireless devices, like UE $120_A$, and such coverage is achieved via a wireless link 115. In an aspect, UE 120 can be a 3rd Generation Partnership Project (3GPP) Universal Mobile Telecommunication System (UMTS) mobile phone.

Within macro coverage cell 105, a femto cell 145, served by a femto access point 130, can be deployed. A femto cell typically covers an area 125 that is determined, at least in part, by transmission power allocated to femto AP 130, path loss, shadowing, and so forth. Coverage area typically is spanned by a coverage radius that ranges from 20 to 50 meters. Confined coverage area 145 is generally associated with an indoors area, or a building, which can span about 5000 sq. ft. Generally, femto AP 130 typically services a few (e.g., 1-9) wireless devices (e.g., subscriber station $120_B$) within confined coverage area 145. In an aspect, femto AP 130 can integrate seamlessly with substantially any packet switched (PS)-based and circuit switched (CS)-based network; for instance, femto AP 130 can integrate into an existing 3GPP Core via conventional interfaces like Iu-CS, Iu-PS, Gi, Gn. In another aspect, femto AP 130 can exploit high-speed downlink packet access in order to accomplish substantive bitrates. In yet another aspect, femto AP 130 has a LAC (location area code) and RAC (routing area code) that is different than the underlying macro network. These LAC and RAC are used to identify subscriber station location for a variety of reasons, most notably to direct incoming voice and data traffic to appropriate paging transmitters.

As a subscriber station, e.g., UE $120_A$, leaves macro coverage (e.g., cell 105) and enters femto coverage (e.g., area 125), as illustrated in environment 100, UE $120_A$ attempts to attach to the femto AP 130 through transmission and reception of attachment signaling, effected via a FL/RL 135; in an aspect, the attachment signaling can include a Location Area Update (LAU) and/or Routing Area Update (RAU). Attachment attempts are a part of procedures to ensure mobility, so voice calls and sessions can continue even after a macro-to-femto transition or vice versa. It is to be noted that UE 120 can be employed seamlessly after either of the foregoing transitions. Femto networks are also designed to serve stationary or slow-moving traffic with reduced signaling loads compared to macro networks. A femto service provider (e.g., an entity that commercializes, deploys, and/or utilizes femto access point 130) is therefore inclined to minimize unnecessary LAU/RAU signaling activity at substantially any opportunity to do so, and through substantially any available means. It is to be noted that substantially any mitigation of unnecessary attachment signaling/control is advantageous for femto cell operation. Conversely, if not successful, UE 120 is generally commanded (through a variety of communication means) to select another LAC/RAC or enter "emergency calls only" mode. It is to be appreciated that this attempt and handling process can occupy significant UE battery, and femto AP capacity and signaling resources as well.

When an attachment attempt is successful, UE 120 is allowed on femto cell 125 and incoming voice and data traffic are paged and routed to the subscriber through the femto AP 130. It is to be noted also that data traffic is typically routed through a backhaul broadband wired network backbone 140 (e.g., optical fiber backbone, twisted-pair line, T1/E1 phone line, digital subscriber line (DSL), or coaxial cable). To this end, femto AP 130 is connected to the broadband backhaul network backbone 140 via a broadband modem (not shown).

It is to be noted that as a femto AP 130 generally relies on a backhaul network backbone 140 for routing and paging, and for packet communication, substantially any quality of service (QoS) can be handled for heterogeneous packetized traffic. Namely, packet flows established for wireless devices (like terminals $120_A$ and $120_B$) served by femto AP 130, and for devices served through the backhaul network pipe 140. It is to be noted that to ensure a positive subscriber experience, or perception, it is important for femto AP 130 to maintain a high level of throughput for traffic (e.g., voice and data) utilized on a mobile device for one or more subscribers while in the presence of external, additional packetized, or broadband, traffic associated with applications (web browsing, data transfer (e.g., content upload), and the like) executed in devices within the femto coverage area (e.g., either area 125 or area 145).

Figure 2A:
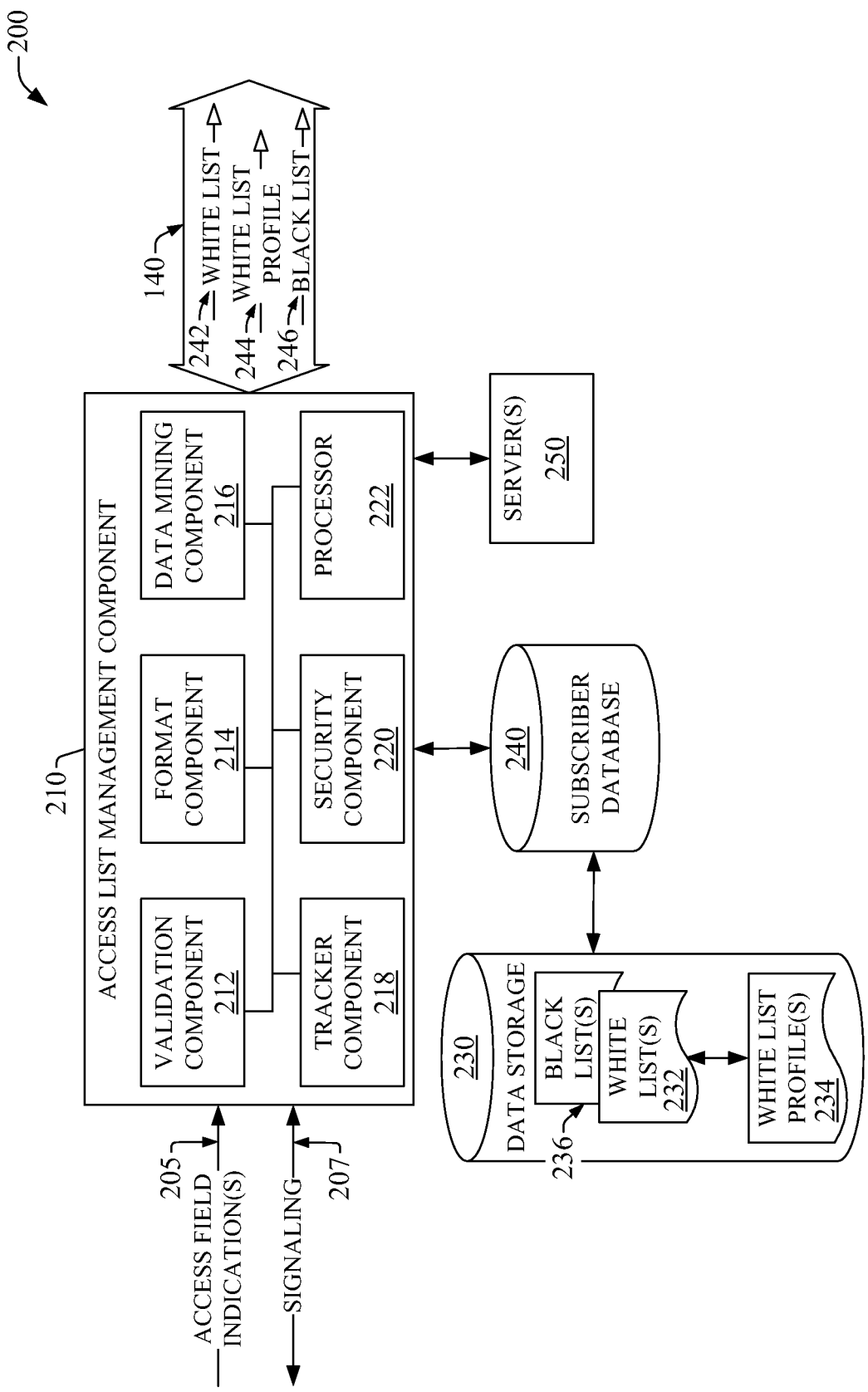
FIGS. 2A and 2B are block diagrams of an example system that facilitates generation of access control list(s) and white profile list(s) to manage access to femto cell coverage, and example white list, black list and access profile, respectively, in accordance with aspects disclosed herein.

FIG. 2A is a block diagram of an example system 200 that facilitates selection of subscribers, and mobile devices linked thereto, through an initial configuration or update, to access coverage from a femto cell, or femto access point; selection can enable or disable coverage for specific subscriber(s) link to specific subscriber station(s). Functionality provided by example system 200 to authorize, permanently or temporarily, or deny or revoke access to specific subscribers, or subscriber station(s), comprise what is herein termed as an access control list(s) (e.g., white list(s) or black list(s))—an instrument for management of access to femto cell coverage. Additionally, in connection with authorization for access to femto cell coverage, example system 200 facilitates generation of a white list profile which includes parameters that control, or facilitate access logic to, femto cell coverage as provided (e.g., granted or denied) through access control list(s) (e.g., white list(s) or black list(s)). Moreover, example system 200 can retain access list(s) (e.g., white list(s) or black list(s)), or white list profile(s), and aggregate such access list(s) and white list profile(s).

In an aspect of the subject innovation, access list(s) (e.g., white list(s) or black list(s)) and white list profile(s) can be relational database tables that include a set of one or more fields for each attribute in the tables. It is noted, however, that other table models (e.g., hierarchical, object oriented) can be employed to define access list(s) and white list profile(s). Various attributes can be defined for access list(s); for example, mobile device identifier attribute, which uniquely identifies the mobile device; public or private attribute, which can be an election flag (e.g., opt-in/opt-out flag) that establishes whether mobile device identifier can be shared among disparate access list(s); device technology attribute(s), which provides information on operation capabilities of mobile device(s) includes within white list(s); and so forth. As an illustration, a device identifier attribute in access list(s) (e.g., white list(s) or black list(s)) can support up to N fields (N a positive integer; e.g., N=50) for unique mobile phone numbers (e.g., MSIDSNs, IMSIs), or any suitable codes (e.g., electronic serial numbers (ESNs), SIM credentials) or tokens that identify a mobile device. Number N of fields can be determined, or configured, by a service operator based at least in part on technical aspects (like network resources, quality of service consideration, macro area of coverage (e.g., metropolitan statistical area (MSA), or rural service area (RSA)) and commercial aspects (such as promotional considerations, mitigation of customer attrition, gains in market share, etc.) of provision of coverage. As an example, N can be subscriber dependent or femto AP dependent; e.g., premium subscriber that consumes substantive volume of data, like prosumers, can have larger N than subscribers that primarily consume voice. It should be appreciated that the magnitude of N can also be determined dynamically, and augmented on a subscriber-need basis within bounds determined by network capacity.

In an aspect of the subject innovation, black list(s) include a single attribute field which uniquely identifies a mobile device, the identified device is denied femto access service. It is noted that while a black list is a realization of an access list, and can be configured by a consumer according to aspects described herein, a black list can be employed as an administrative instrument to deny femto service under various criteria, e.g., lack of payment for service(s), unlawful utilization of a provisioned femto access point, and so forth. Mobile device identified in a black list can operate in "emergency call" mode only.

With respect to white list profile(s) 234, one or more attributes thereon can be associated with a white list. The one or more attributes establish logic for utilization of femto coverage by mobile stations associated identified through a mobile device identifier attribute in a white list. White list profile(s) attribute(s) and values thereof can establish access privileges to femto coverage. In an aspect, prioritization of femto utilization as established through white list profile(s) can be based on user segments, e.g., some users have higher priority than others, in particular, access list management component 210 can rank users allowed in the femto and assign a priority access field in a white list profile. Likewise, white list profile can prioritize services (e.g., voice, data, voice and data) for disparate whitelisted mobile devices. Access management component 210 can allocate, at least in part, different resources or types of services that can be provided to a whitelisted mobile device; for example, access management component can filter guest(s) for specific contents received through specific services; such filtering can be configured through white list access profile(s). Additionally, white list profile(s) can include an access field attribute that indicates access management to convey, via signaling 207, for example, to a device in a white list the service the device is allowed to utilize through femto coverage. Moreover, white list profile also can include an access field attribute that allows to block a mobile device identified in white list(s). In an aspect, white list profile(s) attribute(s) are related to field values, or records, in white list(s) via primary keys (e.g., a unique mobile device identifier) of the white list(s). As an example, for a mobile station catalogued via a respective identifier numeric attribute (e.g., mobile subscriber number integrated digital services network number (MSISDN), international mobile subscriber identity (IMSI) number) in a white list (e.g., white list(s) 232), service attribute(s) in the white list profile (e.g., white list profile(s) 234) can determine at least one of the following. (1) A category of service (e.g., voice only, data only, voice and data), or a class of service, which determines access to specific applications or services such as scheduler, calendar(s), news streaming, authoring tools, gaming, video and music, etc., that is allowed for the mobile station; (2) quality of service configuration, or customization, for mobile device access to femto coverage, such as guaranteed QoS (e.g., guaranteed packet rate, or guaranteed block error rate) rather than best effort delivery; (3) time span of allowed service for the mobile station such as (i) temporary full access to provisioned femto service(s), e.g., full access for a specific time interval such as days (e.g., a relative is on vacation on a house with a provisioned femto AP) or hours (babysitter is on duty), or (ii) temporary restricted access, which can determine access to selected services only within a window of time in a day (voice and data allowed from 9:00 a-6:00 p, or voice allowed after 9:00 p which can facilitate billing schemes already established by an operator/service provider); (4) telecommunication technology allowed for use in a femto cell when the mobile station supports operation through multiple technologies (e.g., GSM, 3GPP UMTS, 3GPP LTE Advanced . . . ); (5) billing aspects for an identified mobile device; and so on.

In an illustrative aspect of the innovation, access list(s) (e.g., white list(s) 232 or black list(s)) and white list profile(s), or any set of numbers, codes or tokens thereon that comprise a set of mobile phones or mobile devices approved for coverage by femto access point (e.g., femto AP 130), can be portable through accounts or billing groups associated with a set of subscribers to a service operator that administers femto AP 130, or a macro network.

Access field(s) associated with access list(s) (e.g., white list(s) or black list(s)) attribute(s) and white list profile(s) attribute(s) can be populated with content(s) received through a set of access field indication(s) 205, which is linked to a set of mobile devices and intended for at least one of access list(s) or white list profile(s). Access field indication(s) can be received from various apparatuses or sources such as a mobile device or a server in a network (e.g., a service network linked to a mobile network platform), and can be embodied in a short message service (SMS) communication, a multimedia service (MMS) communication, an email communication, instant message (IM) communication, an unstructured supplementary service data (USSD) message, or the like. In addition, access field indication(s) 205 can be embodied in lower level signaling such as a set of one or more bits in packet header or in control frames; packets can adopt various formats like, internet protocol (IP), frame relay, or asynchronous transfer mode (ATM). Access field indication(s) 205 can be processed by server(s) 250 that can provide the various services (e.g., email service) that facilitate the embodiments of access field indication(s). For example, a server(s) 250 can be embodied in an email server that administers an email account like towhitelist@provider.domain.com through which a subscriber can convey access field content(s), e.g., a mobile device identifier number, for a white list associated with the subscriber. The email server can extract received access field content(s) for inclusion in access control list(s) (e.g., white list(s) or black list(s)) or white list profile(s).

In addition to access field indication(s) 205, access list management component 210 can receive signaling 207, which can convey directive(s) to remove or add content(s) of access field(s) within an access list (e.g., a white list or black) or within a white list profile. In an aspect, signaling 207 can be received from various apparatuses or sources such as a mobile device or a server in a network (e.g., a service network linked to a mobile network platform), and can be embodied in a SMS communication, a MMS communication, an email communication, IM communication, a USSD message, or the like. In addition, signaling 207 can be embodied in lower level signaling such as a set of one or more bits in packet header or in control frames.

In example system 200, validation component 212 can ensure integrity of data, e.g., content(s) identified through received access field indication(s) 205, related to access list(s) (e.g., white list(s) 232 or black list(s) 236) and white list profile(s) 234; access list management component 210 can receive access field indication(s) 205. In an aspect, validation component 212 can validate (e.g., either accept or reject) a mobile device identifier attribute through one or more check procedures that rely on a set of criteria applied to the received access field indication(s) 205 of the identifier attribute value. At least one of data mining component 216 or tracker component 218 can assist with validation of field content(s) received through access field indication(s) 205. For example, tracker component 218 can monitor changes (e.g., updates) to subscribed service and identifier numbers for served subscribers, while data mining component 216 can gather information related to one or more criterion on the set of criteria, through networked access to subscriber database 240, or substantially any, or any, other database or data storage 230 accessible to a mobile network that facilitates coverage through a femto access point (e.g., femto AP 130) or a macro cell base station. It is noted that data exchange among access data mining component 218 and accessible databases can proceed securely; security mechanism(s) can be provided, in an aspect, by security component 220. The set of criteria can include at least one of the following. (i) Valid mobile device identifier (e.g., wireless device numbers such as MSISDNs, codes or tokens). (ii) Active mobile device identifier, or identifier flagged for update; e.g., received access field indication(s) 205 conveys an identifier field that corresponds to an old phone number that is to be updated to a current number. (iii) Status of election (e.g., opt in) or non-election (e.g., opt out) flags for inclusion in a white list, wherein status is conveyed, for example, via a K-bit word (K is a natural number) within an entry for the mobile device in a subscriber database. (iv) Operational capabilities of the mobile device (e.g., wireless technology utilized by the device such as second generation (2G), third generation (3G), or fourth generation (4G) technologies, radio frequency bands in which the mobile device can receive communications . . . ). (v) commercial standing (e.g., good standing or outstanding bill payments, hotlined mobile device in view of recurring lack of timely payments for service, stolen device . . . ); or the like.

Figure 2B:
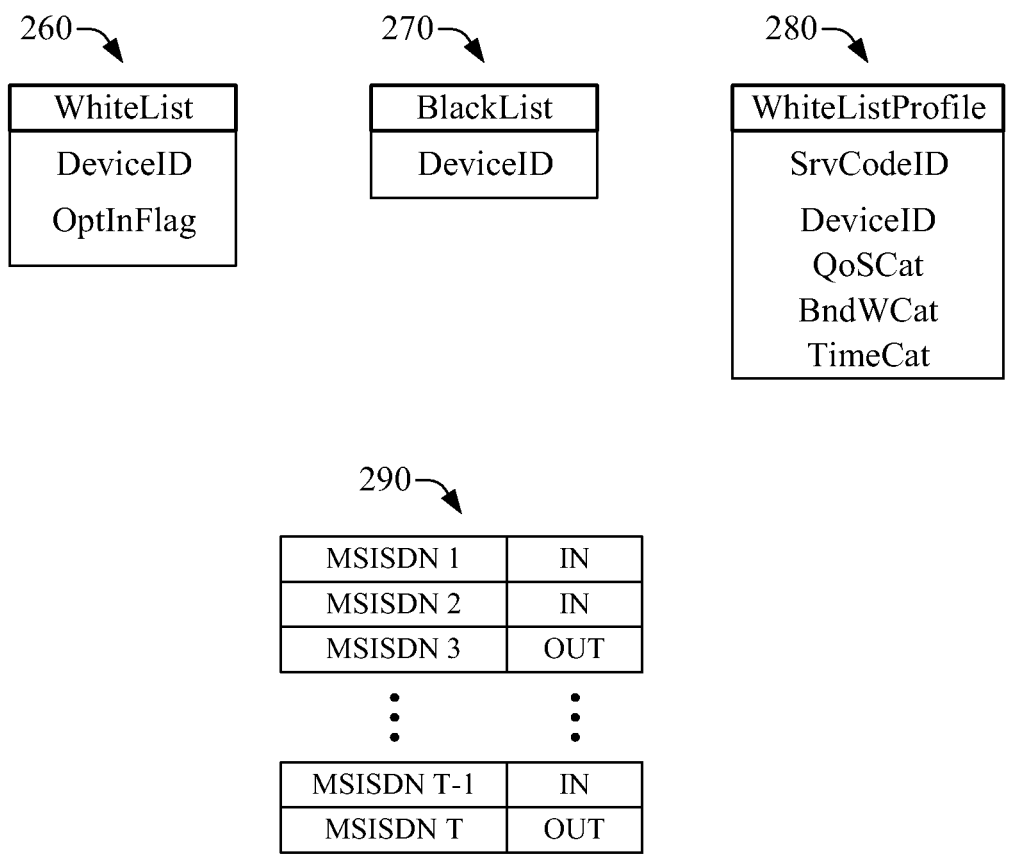

Access list management component 210 can generate at least one of access list(s) (e.g., white list(s) 232 or black list(s) 236) or white list profile(s) 234 based at least in part on valid received access field indication(s) 205. Generated access list(s), e.g., white list(s) 232 or black list(s) 236, and generated white list profile(s) 234 can be retained in data storage 230. It should be appreciated that data storage 230 can be deployed at least in part within a service provider network platform (e.g., macro network platform or femto network platform) that exploits access list management component 210, or in network(s) external to the service provider network platform such as non-mobile network platform(s) (e.g., broadband internet service provider, enhanced 911 service, billing platforms, multimedia services . . . ). Alternatively, or in addition, access list(s) or white list profile(s) can be stored in a subscriber database which is typically linked to the service provider network platform. Example white list 260 and a realization 290, black list 270, and white list profile 280 are presented in FIG. 2B. Example white list 260 includes two access field attributes: DeviceID, which uniquely identifies a device, and OptInFlag which indicates whether a specific device has opted in for dissemination, or inclusion, in disparate white lists; realization 290 of example white list 260 illustrates T (a natural number) access fields populated with MSISDN 1-T for access field attribute DeviceID, and character type access fields for access field attribute OptIn. Example black list 280 includes a single access field attribute DeviceID, while example WhiteListProfile 280 includes five access field attributes: SrvCodeID, a unique identifier for a service profile given by the 4-tuples in the profile; DeviceID which is a foreign key that identifies a device for which service profile code applies; a QoSCat attribute, e.g., conversational; a BndWCat attribute that determines how much bandwidth device identified through DeviceID is allotted; and TimeCat attribute which indicates a time interval during which the attributes are granted.

Access list management component 210, through format component 214, can format access list(s) (e.g., white list(s) 232 or black list(s) 236) or white list profile(s) 234 in accordance with various schemas, such as hypertext markup language (HTML) and extensible markup language (XML) and variants (e.g., state chart XML (SCXML)), that are portable among computing platforms, wireless (e.g., a portable computer or mobile device) or otherwise, and object-oriented computing languages employed by a wireless device such as Delphi, Visual Basic, Python, Perl, Java, C++, and C#, and circuitry programming level languages such as Verilog. Such portability can facilitate straightforward exchange of access list(s) (e.g., white list(s) or black list(s)) among subscribers and related billing groups of a service provider. Extensibility afforded by such formats can facilitate aggregation of access lists (e.g., white lists) and extraction of at least portions thereof, in web-based applications web-based commerce (ecommerce) systems, blogs, peer-to-peer exchange web applications, social networking websites, or the like; it should be appreciated that aggregation and extraction of access lists (e.g., white lists) can be conducted, through at least one of data mining component 216 or validation component 212 in access list management component 210, as a part of access list(s) (e.g., white list(s) or black list(s)) administration at the network level. Additionally, format component 214 can compress (e.g., via non-lossy wavelet-based compression) or index aggregated access list(s) (e.g., white list(s) 232 or black list(s) 236) for efficient storage. Moreover, format component 214 can commit an identifier to an access list (e.g., white list(s) 232) in a network native format (e.g., full-length digit for a MSISDN or IMSI), or via unique identifier code numbers for the device (e.g., ESN, international mobile equipment identity (IMEI), or mobile equipment identification (MEID)). It is noted that subscribers are not generally exposed to such formats. It should be appreciated that a white list and a white list profile can be merged into a single component or entity.

In an aspect of the subject innovation, access management component 210, via data mining component 218 can identify femto access point in a forward manner in order to expand coverage provided to a subscriber. For example, a café in a skating rink that a subscriber regularly visits when taking his/her children for skating practice may have provisioned a femto access point; thus, inclusion of the subscriber into an access control list (e.g., a white list) that manages access to the café's femto access point can be advantageous to the subscriber.

To identify suitable access points, data mining component 218 can employ location information and identify or infer pattern(s) of call (e.g., voice call) activity of a subscriber, and extract an access point based at least in part on the inferred pattern. It is noted that utilization of at least a portion of the information necessary to autonomously determine, or match, a femto access AP for a subscriber, proceeds according to privacy settings established by the subscriber. It should be appreciated that data mining component 218 can infer a set of one or more femto access points of interest based on other data extracted from a set of databases accessible to a service provider. When a femto AP is identified, authorization to update a white list that manages access to femto coverage is requested from an administrator subscriber; it should be appreciated that authorization requests proceed in accordance with privacy settings (not shown) of administrator subscriber(s). When authorization is granted, access management component 210 can negotiate level of access to femto coverage via the identified femto access point. When negotiation ends, access management component 210, via a communication platform (not shown in FIG. 2), can convey at least one of an updated white list or a white list profile.

In accordance with an aspect of the subject innovation, data mining component 351 can utilize artificial intelligence (AI) methods to infer (e.g., reason and draw a conclusion based at least in part on a set of metrics, arguments, or known outcomes in controlled scenarios) patterns of call activity, relevancy of locations associated with the pattern, and/or other features suitable to autonomously identify a desirable femto access point for a subscriber. Artificial intelligence techniques typically can apply advanced mathematical algorithms—e.g., decision trees, neural networks, regression analysis, principal component analysis (PCA) for feature and pattern extraction, cluster analysis, genetic algorithm, and reinforced learning—to historic and/or current data associated with mobile devices served by a mobile network platform at the macro or femto level to facilitate rendering an inference(s) related to the mobile devices.

In particular, data mining component 216 can employ one of numerous methodologies for learning from data and then drawing inferences from the models so constructed, e.g., Hidden Markov Models (HMMs) and related prototypical dependency models. General probabilistic graphical models, such as Dempster-Shafer networks and Bayesian networks like those created by structure search using a Bayesian model score or approximation can also be utilized. In addition, linear classifiers, such as support vector machines (SVMs), non-linear classifiers like methods referred to as "neural network" methodologies, fuzzy logic methodologies can also be employed. Moreover, game theoretic models (e.g., game trees, game matrices, pure and mixed strategies, utility algorithms, Nash equilibria, evolutionary game theory, etc.) and other approaches that perform data fusion, etc., can be exploited in accordance with implementing various automated aspects described herein.

Access management component 210 can convey, via broadband backhaul pipe 140, at least one of generated white list 242, white list profile 244, or black list 246. It should be appreciated that when no access field indication(s) 205 are received, access list management component 210 can convey a default white list 242 with an identifier attribute populated with identifier fields for substantially all, or all, wireless devices provisioned to a subscriber that acquires femto cell service. It should be appreciated that access list management component 210 can reside within a femto access point (e.g., femto AP 130), e.g., within access management component 355. In such a scenario access management component 210 can convey at least one of generated white list 242, white list profile 244, or black list 246 to a memory within the femto access point.

Generation of access list(s) (e.g., white list(s) 232 or black list(s) 236) and white list profile(s) 234 as described in connection with aspects and features of example system 200, provides at least the following three illustrative advantages. (1) Security against devices attempting to hack into the femto AP when networked with it, and support of extensible sharing/networking of the authorization scheme; e.g., white list(s) can be shared. (2) Capacity to determine and customize quality of service (QoS), grade of service, or service experience, for specific authorized subscribers; in an aspect, such capacity enabled or provided via utilization of white list profile(s) 234. (3) Capacity to ensure integrity of data related to access list(s) (e.g., white list(s) 232 or black list(s) 236) and white list profile(s) 234.

It is noted that in example system 200, processor 222 confers at least in part the described functionality of access list management component 210 and components therein. Processor 222 can be configured to execute code instructions stored in a memory (not shown), or a memory component thereon, to provide at least a portion of the described functionality. It should be appreciated that the processor can be a centralized element or be distributed among the above referenced components, server, and platform.

Various illustrative aspects of the subject innovation based at least in part on an access control list(s) (e.g. white list(s) or black list(s)) concept are discussed next. It is to be noted that variations and extensions of such illustrative aspects are possible and are within the scope of the subject innovation.

Figure 3A:
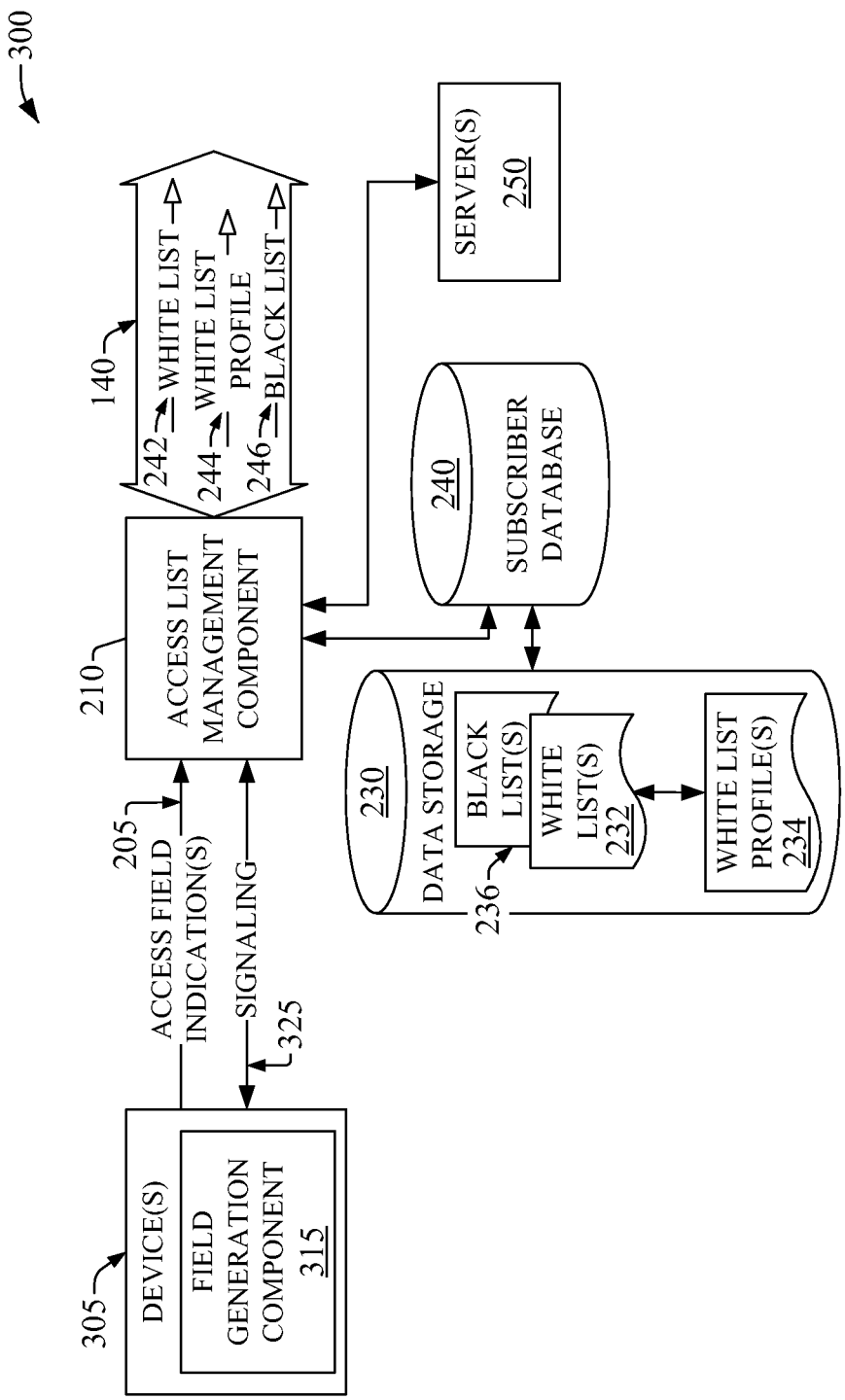
FIGS. 3A-3C illustrate block diagrams of example systems that exploit an access management component to configure or update access control list(s) (e.g., white list(s) or black list(s)) or white list profile(s) according to aspects described herein.
Figure 3B:
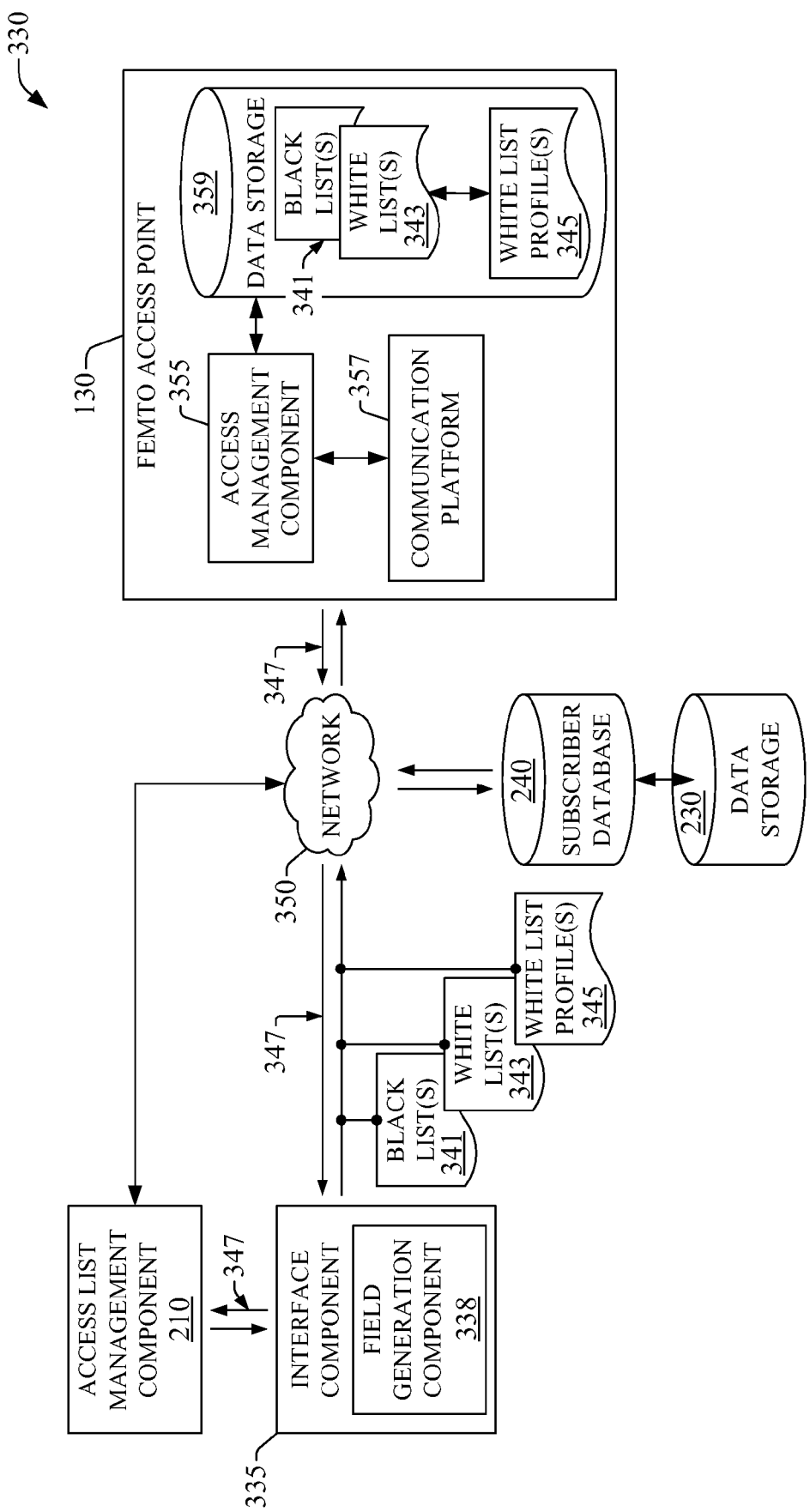
Figure 3C:
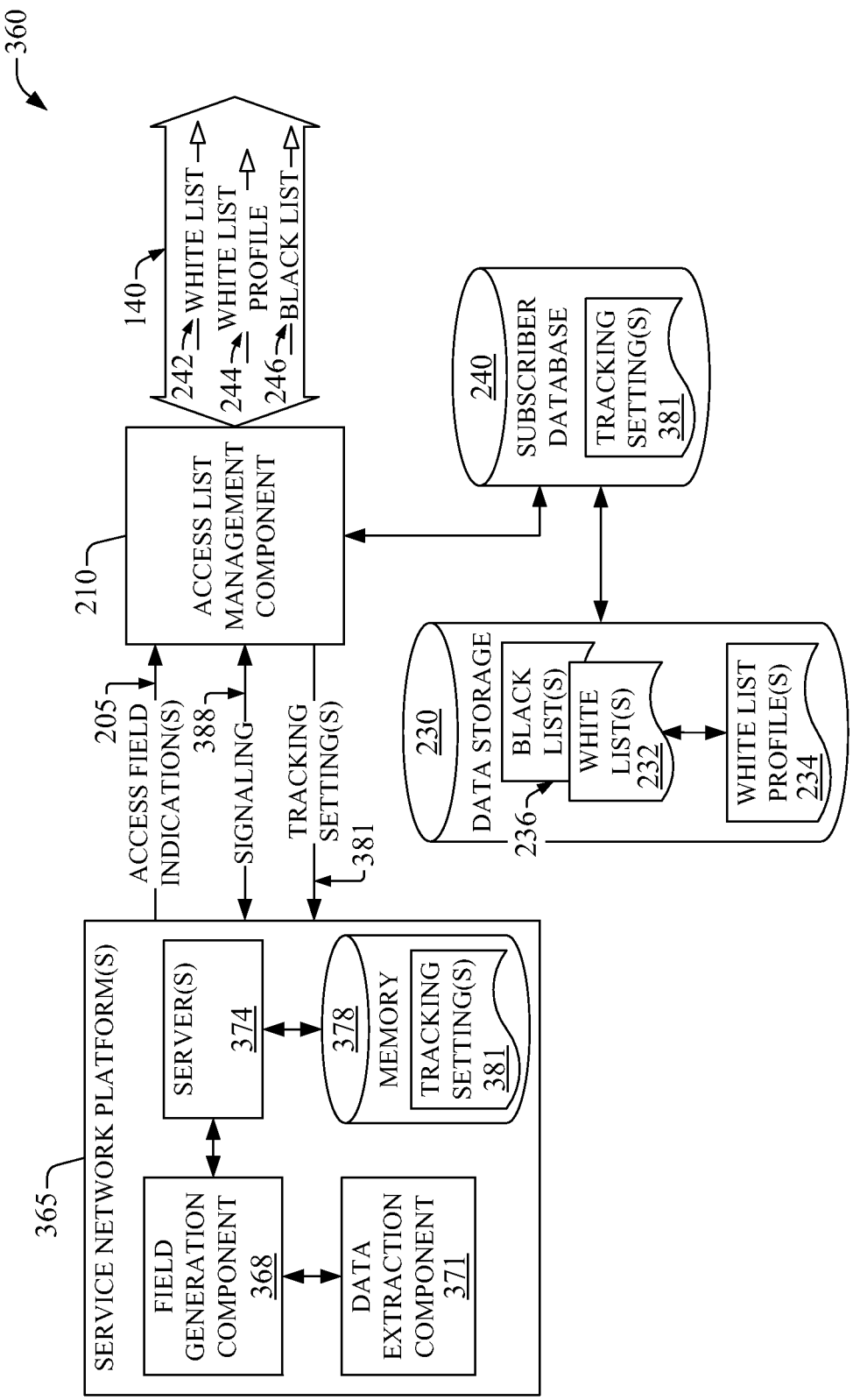

FIGS. 3A-3C illustrate block diagrams of example systems that exploit an access management component to configure or update access control list(s) (e.g., white list(s) or black list(s)) or white list profile(s) according to aspects described herein. In example system 300, mobile device(s) 305 generates and delivers one or more access field indication(s) 205. It should be appreciated that mobile device 305 need not be served, even though it can be served, through femto service to deliver access field indication(s) 205; for instance, such indication(s) can be conveyed out-of-network (e.g., via a visited network or roaming network). In an aspect, field generation component 315 can generate a set of one or more access field indication(s) 205. As described above, access field indication(s) 205 can convey field content(s) for access list(s) attributes or white list profile attribute(s). In addition, mobile device(s) 305 can convey signaling 325 in conjunction with access field indication(s) 205 in order to manipulate access control list(s) (e.g., white list(s) or black list(s)) or white list profile(s), wherein manipulation includes at least one of removal of specific attribute fields, or update of an attribute field. It is noted that removal or update can be effected in one or more access control list(s) or white list profile(s) as indicated in received signaling 325. It is noted that mobile device(s) 305 also can exchange signaling 325 with access list management component 210 to receive authorization to convey access field indication(s) 205; security component 220 can implement, at least in part, secure communication (e.g., password protection, encryption, or the like).

In an aspect, conveyed content(s) can provide a new identifier attribute field for mobile device in order to update a white list 242 associated with a subscriber that operates mobile device(s) 305. As an example, an individual can remotely provide access to femto coverage to a home appliance with wireless capability in order for a technician who services the appliance be able to run diagnostics for the appliance in a remote server and exploit the substantive broadband bandwidth of backhaul backbone that connects the femto AP to a mobile network platform.

In another aspect, access field indication(s) 205 delivered through device(s) 305 can include an updated service attribute field for a white list profile 244 to update the access logic for a mobile device identified in a white list 242 associated with a subscriber that has access to a femto access point. As an example, a trusted visitor in a home (e.g., a grandparent taking care of grandchildren during after-school hours) can be added from a remote location (e.g., workplace) to white list 242 in a temporary session with full privileges to access femto service in the home.

In addition, mobile device 305 can send signaling 325 to request add-on services associated with a device identifier attribute field in a white list 242. Such add-on service can be supported at least in part through server(s) 250. As illustrative, non-limiting scenarios, add-on services can include usage monitoring, configuration of alarms when specific usage of femto service is effected, e.g., a multi-hour download of age inappropriate content(s), chat sessions with sources of unknown reputation, call activity logs, or the like. It should be appreciated that one or more add-on services abide by privacy settings (not shown) associated with the add-on service; validation component 212 can enforce such privacy settings.

With respect to FIG. 3B, example system 330 facilitates manipulation of access list(s), e.g., black list(s) 341, white list(s) 343, and white list profile(s) 345 in accordance with aspects described herein. Interface component 335 facilitates configuration, or setup, of white list(s) 343, and white list profile(s) 345 of wireless mobile station numbers approved for coverage through femto access point 130. It is to be noted that substantially any identification token(s), label(s), or code(s) that identify a subscriber station can be employed as identifier attribute field(s) in white list(s). In addition, interface component 335 can facilitate configuration of black list(s) 341 and white list profile(s) 345.

Through field generation component 338, interface component 335 facilitates generation of access field indication(s) which are conveyed, via network link(s) 347, for example, to access list management component 210. It is noted that network link(s) 347 can be embodied in a Gi reference link. As discussed above in connection with FIG. 2, access list management component 210 can generate access list(s) (e.g., white list(s) or black list(s)) and white list profile(s), which are conveyed to interface component 335. In an aspect, field generation component 338 can receive through interface component 335 one or more values for various attribute fields that define an access list(s) (e.g., black list(s) 341 or white list(s) 343) or white list profile(s) 345. It is noted that interface component 335 can convey attribute fields that are include in the access list(s) or white list profile(s), in order to prompt entry of values for attribute fields (e.g., a mobile device identifier such as a 10-digit mobile directory number, a MSISDN number, an IMSI number, a flag to opt-in/opt-out of inclusion of white list(s), a value that allows specific service categories . . . ).

In example system 330, interface component 335 is networked (e.g., via a wide area network (WAN), local area network (LAN), or backhaul pipe like backhaul network backbone 140) with femto AP 130 and conveys black list(s) 341, white list(s) 343, or white list profile(s) 345 over network link(s) 347. In an aspect, interface component 335 can connect to femto AP 130 via secure login (e.g., virtual private network, secure file transfer, secure copy . . . supported at least in part by network 350. It is noted that network 350 can include one or more networks that facilitate at least in part operation of interface component 335 and communication with femto access point; for example network 350 can include non-mobile broadband internet service provider, local area network, or a mobile network platform (e.g., a core network in a cellular telecommunication environment).

In an aspect, interface component 210 can be a web-based, online graphic user interface (GUI); however, other networked interfaces that facilitate to enter, or configure, white list(s) are possible; for instance, voice or sound commanded interface(s), touch commanded interface(s), biometric commanded interfaces(s), and the like. It is noted that all possible embodiments can include field generation component 338, which can expose an operator that interacts with interface component 335 to prompts and other indicia or gestures to gather values for attribute fields for black list(s) 341, white list(s) 343, or white list profile(s) 345. In example scenarios, it should be appreciated that biometric commanded interface(s) can be employed in environment(s) wherein addition(s) to white list(s) 343 or black list(s) 341, or white list profile(s) 345 is controlled by authorized personnel with specific clearances to add/remove attribute fields, since communication can be classified.

Additionally, in example system 330, a communication platform 255 in femto access point 130 facilitates reception of at least one of black list(s) 341, white list(s) 343, or white list profile(s) 345, and conveys the received at least one of black list(s) 341, white list(s) 343, or white list profile(s) 345 to an access management component 355 that can exploit the received access list(s) (e.g., white list(s) 343) to manage access (e.g., grant, deny, or adjust or modulate) to coverage provided by femto AP 130. The received at least one of black list(s) 341, white list(s) 343 or white list profile(s) 345 can be stored in data storage 359 in the femto AP 130; even though white list(s) 220 and white list profile(s) 222 can be stored in disparate network components like a network component (e.g., subscriber database 240 or data storage 230) administered by a service operator. In addition, interface component 335 can access a subscriber database 240 through network 250, in order to extract identification numbers or identifiers, codes, tokens, or labels for subscribers/subscriber stations that can be entered in a access list(s) (e.g., black list(s) 341, white list(s) 343) or white list profile(s) 345. It is noted that in an additional or alternative scenario, access management component 355 can comprise access list management component 210, in which scenario access list(s) or white profile list(s) can be generated within the access management component in accordance with aspects described herein.

FIG. 3C illustrates an example system 360 for generating access list(s) or white list profile(s) through transactions in a server that meet specific criteria in accordance with aspects described herein. In example system 360, to provide access list management component 210 with access field indication(s) to update access list(s) (e.g., black list(s) 236 or white list(s) 232) or white list profile(s) 234, tracking setting(s) 381 are configured and retained in subscriber database 240, and conveyed to service network platform(s) 365. In an aspect, tracking settings can be generated autonomously (e.g., via machine learning methods) or can be received at least in part form a subscriber; tracker component 218 can facilitate generation of tracking settings 381. Tracking setting(s) 381, which also is retained in memory 378, establishes criteria for tracking a set of transactions in server(s) 374. Such transactions can include online or offline transaction(s) related to commerce (e.g., hotel reservation, airfare purchases); social networking; content dissemination (e.g., blogs, chat rooms); scheduling services (e.g., meeting organizing, appointment(s) in medical clinic, appointment(s) in hair salon); or the like. Tracking criteria 381 includes at least a first criterion that establishes a server or service to be tracked, and a second criterion which discriminates among transactions that include a party that operates a femto access point, or provides femto service, in connection with the transactions. When a transaction meets one or more of tracking criteria 381, tracker component 218 can receive signaling 388 indicating accordingly. Upon receiving signaling 388 that provides information related to a provisioned access point, either in a commercial setting or a residential environment, tracker component 218 can request an access field indication, e.g., a device identifier attribute, in order to update an access list (e.g., a white list) or a white list profile linked to the femto access point.

As an example, a transaction that meets the first criteria is a response to a web-based invitation to an event in an individual's house in which the individual has access to femto cell coverage. When the scheduling service website is included in a tracking list within tracking settings 381, signaling 388 is conveyed to server(s) 374 that facilitates operation of the website when the web-based invitation to the event is accepted, the signaling 388 includes directive(s) to extract data related to the party that has accepted the invitation. To the extent that privacy (e.g., established through a privacy profile (not shown), or ensured via a prompt (not shown) to provide data) allows it, data extraction component 371 gathers information on the party that accepted an invitation and delivers the data to a field generation component 368 that produces content(s) for attribute fields that can be entered in access list(s) (e.g., black list(s) 236 or white list(s) 232) or white list profile(s) 234. Such content(s) can be delivered to access list management component via access field indication(s) 205.

As a result of the tracking and data extraction, the party that indicated attendance to the event, can be added to a white list for femto coverage in the location of the event; an updated white list 242, and white list profile 244, can be conveyed to the femto access point provisioned to the event's host.

It is noted that in example systems 300, 330, and 360, respective processors (not shown) confer at least in part the functionality of the described components and platform(s). Processor(s) can be configured to execute code instructions stored in a memory (not shown), or a memory component thereon, to provide at least a portion of the described functionality. It should be appreciated that the processor can be a centralized element or be distributed among the above referenced components, server, and platform.

In contrast to management of access authorization via femto access point 130, configuration (e.g., setup or update) of access list(s) (e.g., black list(s) 341, white list(s) 343 (registration authorization for femto coverage)) and white list profile(s) 345 through network mechanisms (e.g., interface component 210) provides at least the following advantages. It is to be noted that the following advantages are illustrative and not limiting, as other advantages associated with white list(s) 220 are possible and are intended to lay within the scope of the innovation(s) as described in the subject specification. (1) Access through a networked interface (online or otherwise) reduces provisioning lead time and provides a functionality for customers to update and personalize femto AP autonomously (e.g., free of interaction with technical support entities) at substantially any time. (2) Security against devices attempting to hack into the femto AP when networked with it, and support of extensible sharing/networking of the authorization scheme; e.g., white list(s) can be shared. (3) Networked interface (online or otherwise) provides a superior, rich customer experience substantially free of requirement(s) to understand/interpret femto AP programming interface or configuration nomenclature. (4) End user(s) can manage (e.g., remove select covered numbers, or add additional numbers for coverage up to an allotted amount (e.g., upper bound N) for white list(s) associated with the user. (5) Capacity to determine and customize quality of service (QoS), grade of service, or service experience, for specific authorized subscribers; in an aspect, such capacity enabled or provided via utilization of white list profile(s) 234. (6) Capacity to ensure integrity of data related to access list(s) (e.g., white list(s) 232 or black list(s) 236) and white list profile(s) 234.

Figure 4:
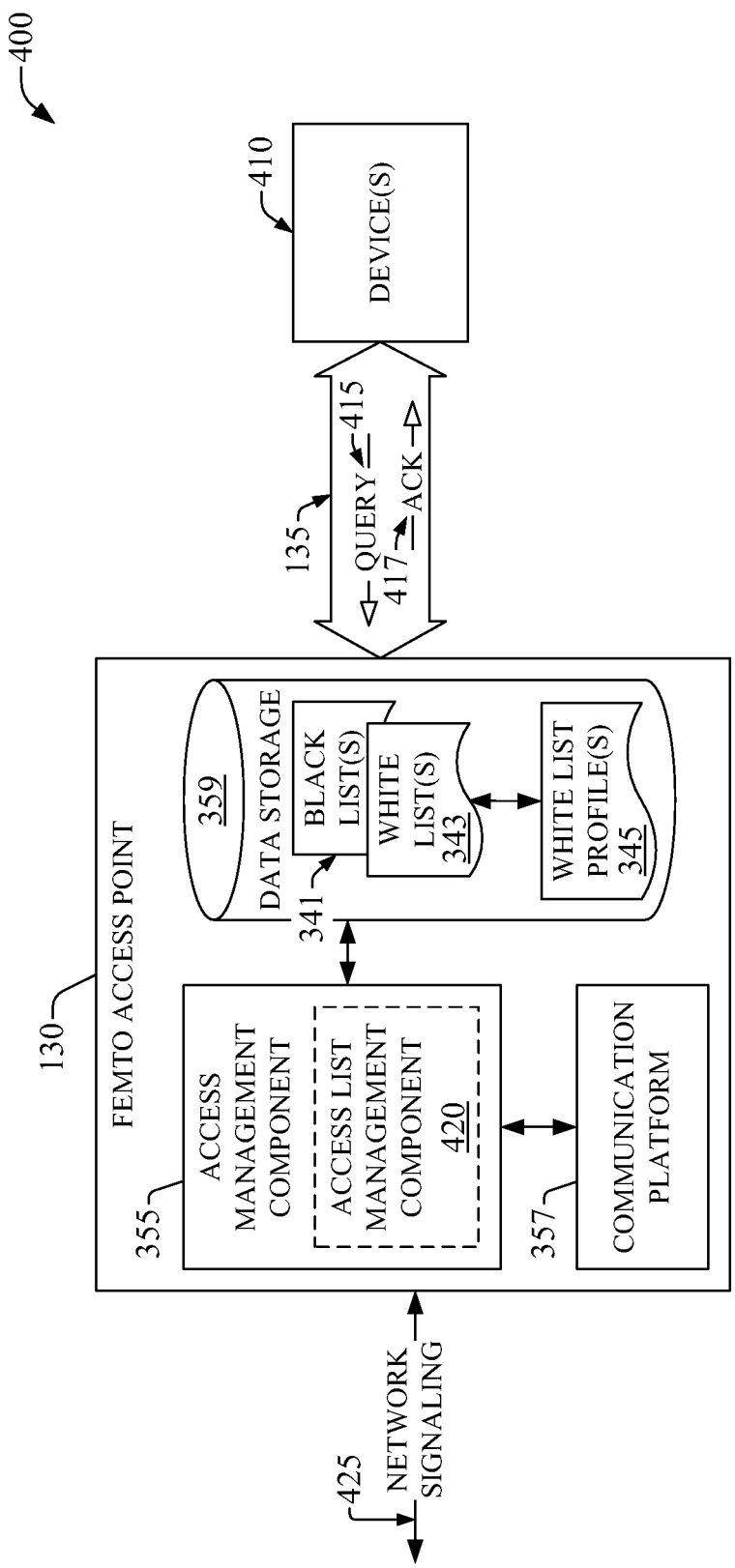
FIG. 4 is a block diagram of an example system that facilitates addition to a white list of mobile device identifier attribute fields on an ad hoc basis in accordance with aspects described herein.

FIG. 4 is a block diagram of an example system 400 that facilitates addition to a white list of mobile device identifier attribute fields on an ad hoc basis in accordance with aspects described herein. In example system 400, device(s) 410 can convey, e.g., through signaling, a request or query 415 to access coverage of femto AP 130; query 415 can be delivered in a control channel when femto AP 130 operates in wireless broadband mode or in a management frame or packet when in-band operation of femto AP 130 is implemented. It should be appreciated that a multi-mode chipset can operate, at least in part, communication platform 357 in order for it to receive and convey signal in various telecommunication mode(s). Query 415 can be received by communication platform 357, and access management component 355 can be configured to allow or reject the request; allowance of rejection of a request can be based on various metrics, such as security, type of device, profile of subscriber linked to the device that requests access, and so on. Configuration to allow or reject the request includes exchange of network signaling 425 in order to access relevant information associated with mobile device 410. In an aspect, access management component 420, which can operate in substantially the same manner as access list management component 210 and includes substantially the same components therein, can facilitate validation of requester device(s) 410 based upon the aforementioned metrics.

Upon allowance of a request (e.g., query 415), access management component 235 can query for available slots, or attribute fields, to be filled in white list(s) 343 associated with account(s) served by femto AP 130. When memory space necessary to include an identifier attribute field value is available for a subscriber station identifier number (e.g., MSISDN, IMSI, ESN, IMEI), code or token, query 415 can further probe whether access is allowed on a permanent, or temporary basis (e.g., to reduce risk exposure to security problems). Characteristics of femto coverage allowance can be set or pre-set through access management component 355 through determination of white list(s) 343 and associated white list profile(s) 345. In an aspect, white list profile(s) 345 can dictate access privilege(s) for an allowed requester mobile device 410 in accordance with default attribute field values in white list profile(s) 345, which can be configured through access list management component 420 at a time femto access point 130 is provisioned. As an example, a default white list profile can allow limited service (e.g., only voice) to requester device(s) 410, or it can customize attribute fields in the default white list profile based at least in part on information gathered in connection with requester device(s) 410. Subsequent to allowance and examination of information related to relevant white list(s) 343, access management component 355 updates white list(s) 343, and related white list profile(s) 345, stored in data storage 359, to reflect the approved request for femto coverage. Upon an identifier for requester device(s) 410 is entered in white list(s) 343, an acknowledgment (ACK) 417 is delivered to device(s) 410 to indicate addition to white list(s) 343 and femto service privileges accorded via white list profile(s) 345. It is to be noted that access and update of collected subscriber identifier numbers (e.g., MSISDN, IMSI), codes, or tokens, also can be implemented through network-based white list database(s), via at least in part network signaling 425. It is to be noted that query 415 can be conveyed via an online GUI (e.g., interface component 335); an email message; a SMS communication; a MMS communication; USSD (or * and # codes) messaging; a voice mail, in order to utilize recognition as a security layer prior to grant access to femto AP coverage; a web prompt; or the like.

An illustrative, non-limiting advantage of example system 400 is that it provides an enhanced end user experience with a direct, clear mechanism to add new mobile device identifiers in white list(s), and thus encourages use of the femto access point 130, and avoids time spent on edition of white list(s) through a networked interface (e.g., interface component 210) like an online interface which typically takes time, a minimum degree of technological savvy, for the end user to access to the Internet and log on in a secured interface, for example.

It should be appreciated that substantially any wireless device within coverage area of femto AP 130 (e.g., area 125) can request access without intervention of a subscriber that operates femto AP 130, and who has previously entered a set of subscriber station numbers (e.g., MSISDNs, IMSIs), codes or tokens, via a networked interface (e.g., interface component 335), for example. Alternatively, or in addition, a request for access (e.g., query 415) can be prompted by a device utilized by a subscriber that operates the femto AP. Further a request for access can be effected by the femto AP, through an access management component like component 355, for example. When a request is granted, a secure tunnel can be established from the device/client through the femto cell's internet protocol (IP) connection or the default connection of a radio access network (RAN) if the IP connection is not available. Secure layers including utilization of the femto cell's virtual private network (VPN) and/or USSD messaging would ensure that the transaction related to edition or manipulation of white list(s) 343, or white list profile(s) 345, is in fact secure. In an aspect, a security component within access management component can facilitate at least in part the secure communication.

As an example, a temporary visitor (e.g., a relative on vacation) or employee (e.g., a babysitter) who is coming over to a location served by a femto access point (e.g., femto AP 130) for a limited period of time, can be provided with coverage via the femto AP by a subscriber that operates the femto cell so the employee can perform, at least in part, his work activities (e.g., provide updates on behavior of children, be contacted reliably through a mobile device . . . ) through utilization of the femto access point. In case the subscriber fails to know identifier numbers (e.g., MSISDNs, IMSIs), codes, or tokens for mobile devices the employee can utilize, and the subscriber is not interested to go through the process of requesting and entering the numbers (e.g., MSISDNs, IMSIs), codes or tokens via a networked interface (e.g., interface component 335) to allow coverage for the limited period of time the employee performs work, the employee (e.g., babysitter) can convey a request (e.g., query 415) for access to femto coverage directly from the employee's device when in range of the femto access point (e.g., within area 125).

Figure 5:
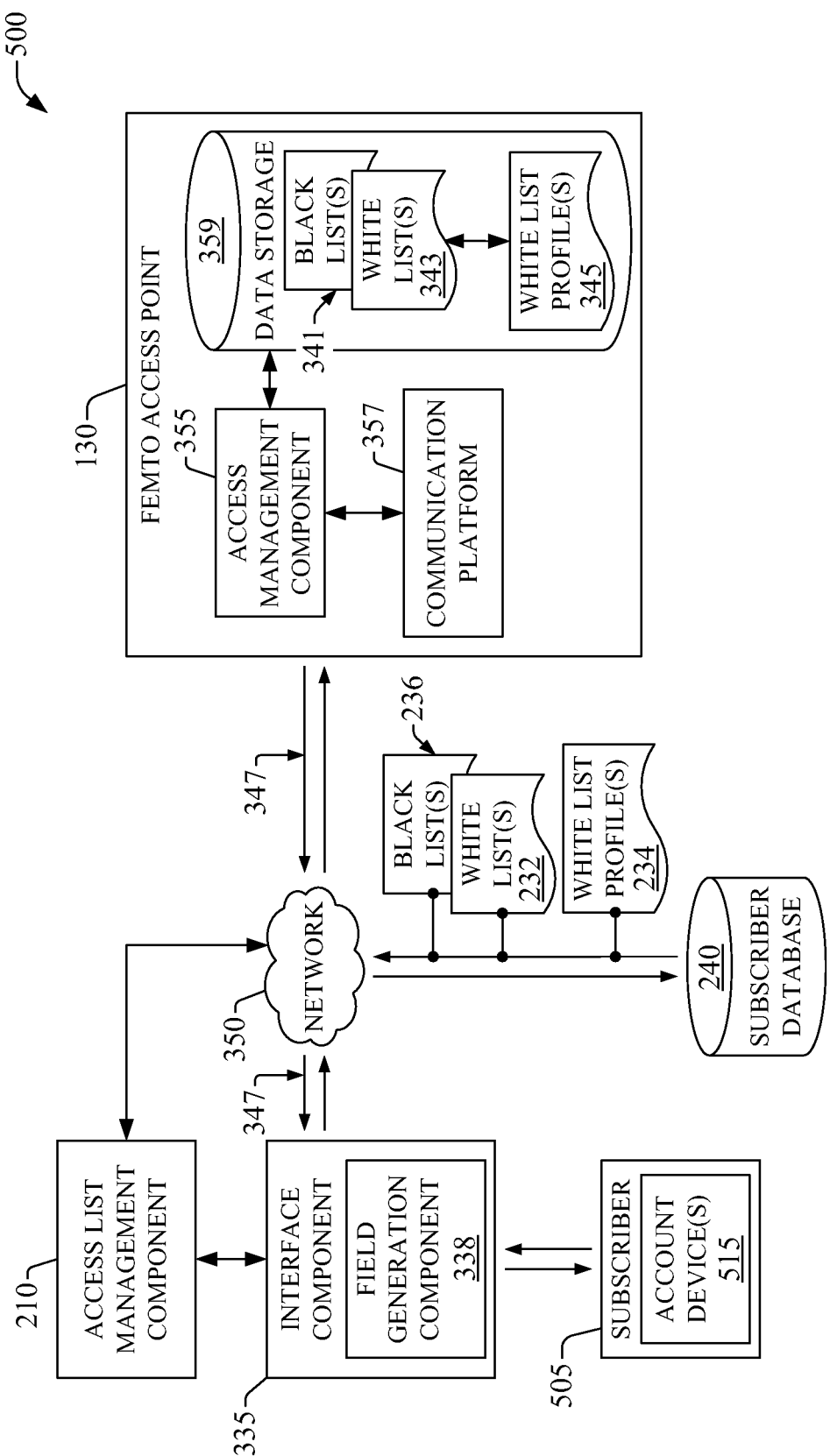
FIG. 5 is a block diagram of an example system that facilitates automatic population of access list(s) (e.g., white list(s) or black list(s)) and generation of white list profile(s) in accordance with aspects described herein.

FIG. 5 is a block diagram of an example system 500 that facilitates automatic population of access list(s) (e.g., white list(s) or black list(s)) and generation of white list profile(s) in accordance with aspects described herein. In example system 500, a subscriber 505 who utilizes account device(s) 515, can provision femto AP 130 and associate account device(s) 515 with a service account via networked interface component 335 (e.g., an online account management system) which can look up into substantially all subscriber station(s) identifier numbers (e.g., MSISDNs), codes or tokens associated with the service account, and automatically populate access list(s) (e.g., white list(s) 232 or black list(s) 236) with the extracted subscriber station(s) numbers, codes or tokens. Account device(s) 515 is part of a subscriber's service account, which can be an account for femto service, and/or macro service, wherein one or more account consumers are billed in accordance to the same billing scheme (e.g., voice and data rating, price point(s) for add-on applications, price point(s) for store on-the-cloud . . . ). As an example, the set of account devices 515 can include handsets and phone numbers (e.g., an IMSI number) that identify the handsets, or cards for wireless service (e.g., subscriber identity module (SIM) cards). It is noted that subscriber 505 can generally access the 10-digit mobile subscriber identification number provided by a network operator, rather than full-length identifier numbers (e.g., identifier field attributes) for account device(s) 515.

Subscriber 505, via interface component 335, can remove or add subscriber station(s) numbers (e.g., MSISDNs, IMSIs), codes, or tokens, extant in pre-populated white list(s) 232; additional edits can be performed as well, based at least in part on the complexity of white list(s) 232 and desired access privileges to femto coverage, provided by femto AP 130, that are to be conferred to whitelisted (e.g., included in white list(s) 232) mobile devices as dictated by white list profile(s) 234. In an aspect, to pre-set white list(s) 220, networked interface component 335 accesses information stored in subscriber database 260 through network 230 which can include information technology systems of a service provider, and data storage related to service network(s) (e.g., internet protocol (IP) multimedia subsystem (IMS)) that provide services to a mobile network platform administered by the service provider. Subscribers that present election flags that decline inclusion in white list(s) are not provided for subscriber 505 to browse. Additionally, to further ensure privacy, partial identifiers in conjunction with a selector component (not shown) can be provided to subscriber 505 to provide access field indication(s) (e.g., identifier attribute fields) associated with mobile device that opted in to access list management component 210. As discussed above, white list(s) 220 and white list profile(s) 222 are conveyed through network 350 via network link(s) 347 to femto access point 130 and retained therein; communication platform 255 receives white list(s) 220, and access management component 355 stores access list(s) (e.g., white list(s) 343 or black list(s) 341) and white list profile(s) 345 in data storage 359.

Interface component 335 can prompt, or query, subscriber 505 in connection with establishment of access list(s), e.g., white list(s) or black list(s), and receive responses associated thereto. Prompt(s) can be generated by field generation component 338, or a provisioning server (not shown) associated with access list management component 210. In an aspect, prompts are directed to collection of subscriber preferences in connection with configuration of access list(s) (e.g., white list(s) or black list(s)) for the set of account devices 515 and identifier attribute fields thereof that can be provided by subscriber 505. Field generation component 338 also can prompt subscriber 505 to provide content(s), e.g., parameter(s), for attribute field(s) that determine characteristics of service (e.g., temporary access, permanent access, specific services . . . ) to be provided to account device(s) 515 entered in an access list (e.g., white list(s) 232).

Illustrative advantages provided by example system 500 are (a) reduced femto cell provisioning lead time, and (b) immediate utilization of a femto cell with mobile numbers that belong to a same service account, with the ensuing billing simplifications (e.g., bundle pricing, voice credits reutilization or transfer among whitelisted (e.g., committed to a white list(s)) numbers, etc.); operation monitoring capabilities (e.g., a parent can monitor usage of voice and data services through femto AP 130 of a child) which can be set through parameter(s) in white list profile(s) such as white list profile(s) 222; enhanced indoor wireless coverage; and so forth; whether subscribers of such numbers subscribe to the femto cell or a feature application, or code, that delivers a femto cell service.

It is noted that in example system 500 a processor (not shown) can confer at least in part the described functionality of the various components or platform(s) in the example system 500, and components therein, included aforementioned systems. The processor can be configured to execute, and execute, code instructions stored in a memory (not shown), or a memory component thereon, to provide at least a portion of the described functionality. It should be appreciated that the processor can be a centralized element or be distributed among the various referenced systems, component, networks, and platform.

Figure 6:
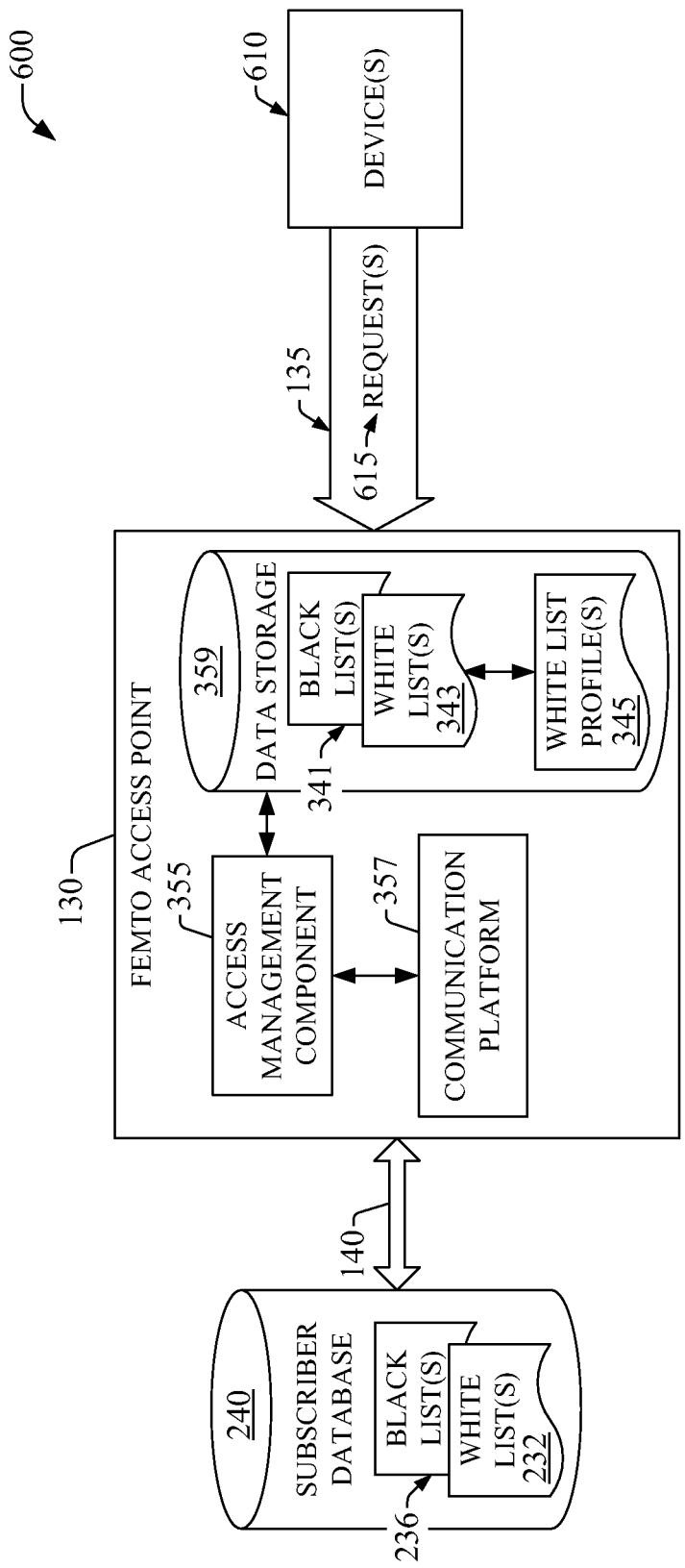
FIG. 6 is a block diagram of an example system that tracks subscriber station identifier attribute fields associated with access list(s) (e.g., white list(s) or black list(s)) on record with a femto service provider in accordance with aspects of the subject innovation.

FIG. 6 is a block diagram of an example system 600 that tracks subscriber station identifier attribute fields (e.g., MSISDNs, IMSIs), codes or tokens, associated with access list(s) (e.g., white list(s) or black list(s)) on record with a femto service provider in accordance with aspects of the subject innovation. When a subscriber (e.g., subscriber 505), or end user, that operates mobile device(s) 610 cancels an account or subscription with a wireless service provider or changes an identifier number, code, or token, associated with mobile device(s) 610 and that serves as an identifier attribute field in white list(s), the subscriber can convey a request 615 via mobile device(s) 610 to remove the identifier number thereof from substantially all, or all, white list(s) 232 on record in a subscriber database 240 or substantially any other database available to a service provider that contains information on service subscribers. It should be appreciated that request(s) 615 can be conveyed as signaling in a control channel or management frame for control communication with femto access point 130. In an aspect, access management component 225 can convey an indication to a mobile wireless platform (e.g., a core network), via backhaul pipe 140, to update white lists (e.g., white list(s) 232) associated with a subscriber linked to device(s) 610 in accordance to request(s) 615. It is noted that local records of white list(s) 220 are also updated as a result of request(s) 615; local update takes place in all femto APs that include white list(s) that comprise mobile device 610 identifier number that is cancelled.

Additionally, or alternatively, when an end user changes mobile or subscriber station number, code or token, (e.g., after relocation to a new area code, or the like), request(s) 615 can be delivered to femto access point 130 to automatically update substantially all, or all, white list(s) 232 on record that include mobile device 610 identifier number, code, or token. Access management component 355 can deliver signaling via backhaul pipe 140 to a mobile network platform to update white list(s) 620 records in subscriber database 230. It is noted that local records of white list(s) 343 in all femto APs that include white list(s) that comprise mobile device 610 identifier number that is updated.

An illustrative advantage of such on-request automatic update of white list(s) 232, and local white list(s) 343, is ease of use for end users to maintain current white lists at the network level and local, e.g., femto AP 130, level without a need to track each of the end user's subscriber station number, code, or token associated with the white list(s) 232. In addition, updated white list(s) 232 and white list(s) 343 maintain the value proposition of the femto cells for end users and service operator by a seamless move of traffic off of the macro network (e.g., a WAN) to femto network(s).

In view of the example systems described above, example methodologies that can be implemented in accordance with the disclosed subject matter can be better appreciated with reference to flowcharts in FIG. 7-13. For purposes of simplicity of explanation, the example methodologies, or methods, are presented and described as a series of acts; however, it is to be understood and appreciated that the claimed subject matter is not limited by the order of acts, as some acts may occur in different orders and/or concurrently with other acts from that shown and described herein. For example, it should be understood and appreciated that a methodology, or method, could alternatively be represented as a series of interrelated states or events, such as in a state diagram, or interaction diagram. Moreover, not all illustrated acts may be required to implement a methodology in accordance with the subject specification. Additionally, it is noted that two or more methodologies, or methods, can be enacted in conjunction. Furthermore, it should be further appreciated that the methodologies, or methods, disclosed hereinafter and throughout this specification are capable of being stored on an article of manufacture to facilitate transporting and transferring such methodologies, or methods, to computers for execution by a processor or for storage in a memory.

Figure 7:
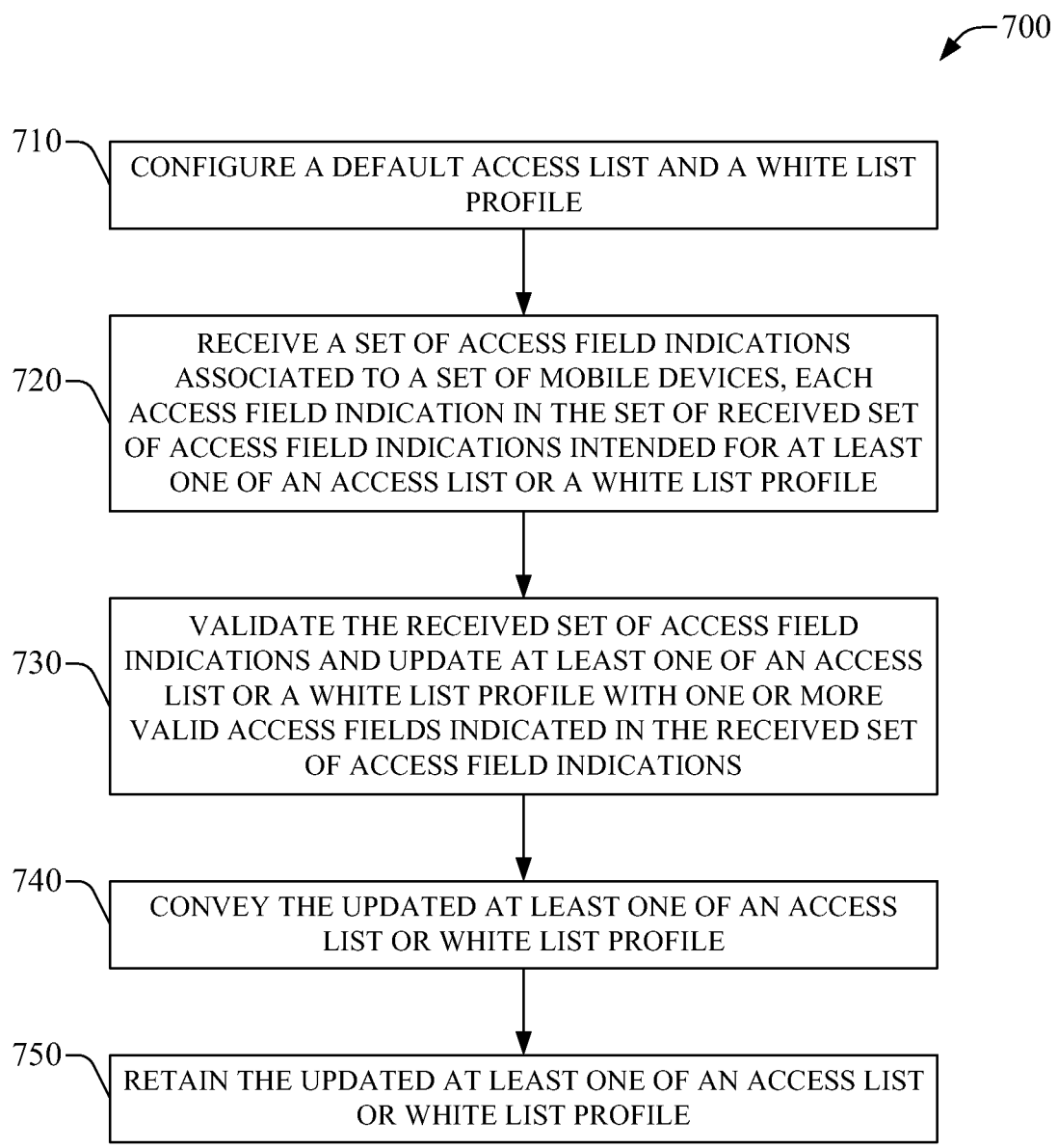
FIG. 7 is a flowchart of an example method for updating an access list (e.g., a white list or black list) and a white list profile according to aspects described herein.

FIG. 7 is a flowchart of an example method 700 for updating an access list (e.g., a white list or black list) and a white list profile according to aspects described herein. The subject example method 700 can be enacted by a component within a mobile network platform (e.g., a core network in cellular technologies such as 3GPP UMTS, 3GPP Long Term Evolution (LTE), 3rd Generation Partnership Project 2 (3GPP2) Ultra-Mobile Broadband (UMB)). At act 710 a default access list and default white list profile are configured. Configuration of an access list can include populating a set of access fields and committing the access list (e.g., a white list or a black list) to memory (e.g., a subscriber database). Default access field values for a white list can include a single field that identifies a mobile device for a subscriber that provisioned a femto access point for which the white list is intended. For a black list, default access field values can include a NULL descriptor and thus no mobile device is explicitly denied access to a femto access point. With respect to a default white list profile, each mobile station associated with an access field that identifies the mobile station in a white list related to the default white list profile is allowed full access to femto service or coverage; the full access dictated by a service plan acquired by a subscriber for which the femto AP is provisioned.

At act 720, a set of access field indications associated to a set of mobile devices is received, each field indication in the received set of field indication is intended for at least one of an access list or a white list profile. The set of access field indications can convey at least in part a set of identifiers, or identification numbers, for each mobile device in the set of mobile devices; the identifiers include MSISDNs, IMSI numbers, or codes or tokens that uniquely identify a mobile device at the hardware level, such as ESN, IMEI, MEID or the like. In addition, access field indications can convey access field values that establish access privileges to femto coverage; privileges can include type of service, time span of coverage, technologies allowed to be employed within coverage area, etc. More particularly, access fields that determine coverage privileges can determine at least one of time intervals for an identified mobile device to access femto coverage; privileges to access voice and data services provided through a provisioned access point that utilizes access list(s) to provide coverage, wherein the privileges dictate degree of access to a service such as QoS profile (e.g., best effort or guaranteed quality of service); allocated bandwidth; preemption profile or relative priority of access to service (e.g., video streaming, sound streaming, voice . . . ) for various mobile devices in a white list, emergency calls are not preempted; or the like.

At act 730, the received set of access field identifications is validated and at least one of an access list or a white list profile are updated with one or more valid access fields indicated in the received set of access field indications. In an aspect, validation includes at least one of verifying a mobile device associated with a field that identifies the mobile device is flagged to opt in for inclusion in femto access service, or identifying commercial standing (e.g., outstanding bill payments, hotlined mobile device, stolen device) of the mobile device associated with the one identifier allows the one identifier to be entered in a white list.

At act 740, the updated at least one of an access list (e.g., a white list or a black list) or white list profile is conveyed. In an aspect, the access control list or white list profile are conveyed to a provisioned femto access point. At act 750, the updated at least one of an access list (e.g., a white list or a black list) or white list profile is retained. The access control list or white list profile can be retained in a subscriber database or in data storage, which can be associated with at least one of a network platform that provides telecommunication service(s) (e.g., femto or macro coverage) or one or more disparate networks linked to the network that provides telecommunication service(s). Data storage can be localized within a single network or distributed among various networks.

Figure 8A:
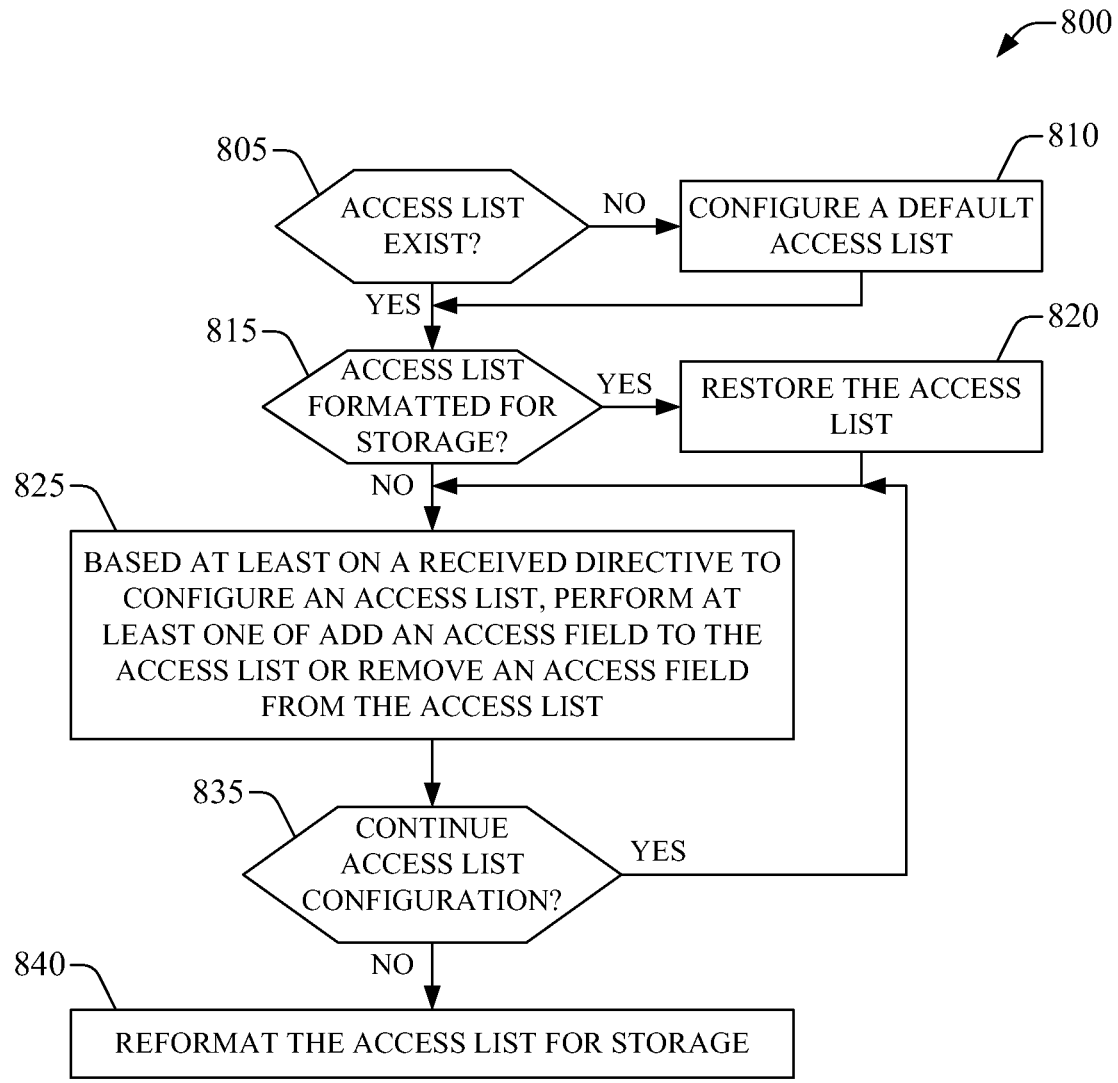
FIGS. 8A and 8B present, respectively, flowcharts of example method for updating an access list (e.g., a white list or a black list) and a white list profile according to aspect of the subject innovation.
Figure 8B:
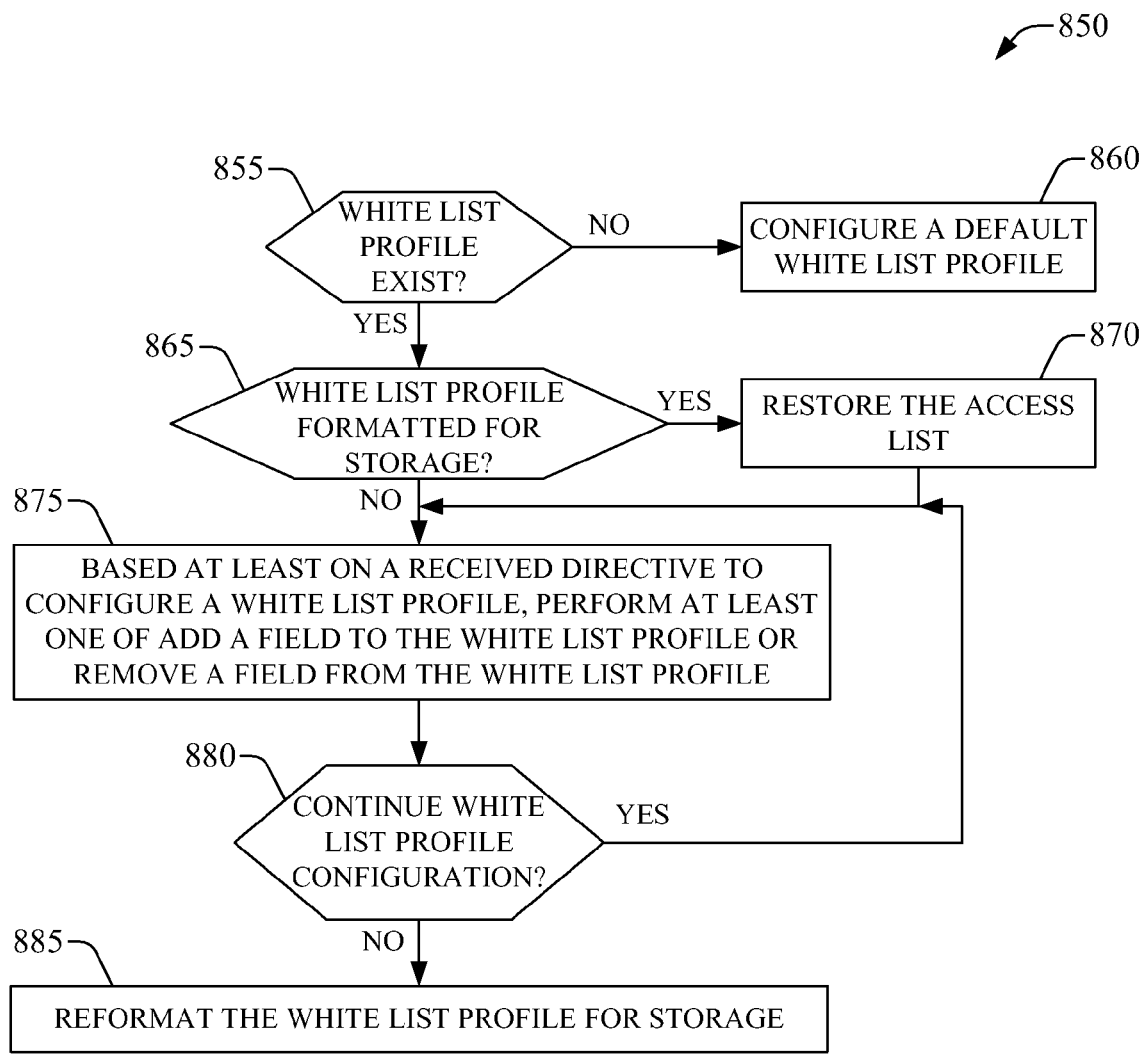

FIGS. 8A and 8B present, respectively, flowcharts of example methods 800 and 850 for updating an access list and a white list profile according to aspect of the subject innovation. The subject example methods can be enacted by a component (e.g., access list management component 210) within a mobile network platform. It should be appreciated that example methods 800 and 850 can be enacted concurrently when a white list and a white list profile are merged into a single component or entity in memory. At act 805 it is checked whether an access list exists. In the negative case a default access list is configured at act 810 and flow is directed to act 815, which is enacted when the outcome of act 805 is positive and probes whether an existing access list is formatted for storage. In an aspect, format for storage of an access list can include various representations such as binary format, wavelet compressed format, indexed representation, or the like. Such storage formats are advantageous particularly when access lists (e.g., white lists) for several ($10^4$-$10^6$) femto access points are aggregated or cross-linked as a result of sharing access lists. When outcome of act 815 is positive, the access list is restored and flow is directed to act 825. Conversely, at act 825, based at least on a received directive (e.g., signaling 325, signaling 207, or request(s) 615) to configure access list, or update access list, at least one of add an access field to the access field list or remove an access field from the access list. It should be appreciated that addition or removal of an access field in an access field can be dynamic in that memory is dynamically allocated upon addition and dynamically deallocated upon removal of an access field. Alternatively, field content(s) can be added to or removed from a static memory allocation for the access list. At act 835, it is checked if access list configuration is to be continued. In the affirmative outcome, flow is directed to act 825. Conversely, flow is directed to act 840 in which the access list is reformatted for storage; for instant, the updated list is aggregated with a set of access lists and recompressed.

With respect to FIG. 8B, in example method 850 in connection with white list profile update, at act 855 it is checked whether a white list profile exists. In the negative case a default white list profile is configured at act 860 and flow is directed to act 865, which is enacted when the outcome of act 855 is positive and probes whether an existing white list profile is formatted for storage. In an aspect, format for storage of an access list can include various representations such as binary format, wavelet compressed format, indexed representation, or the like. Such storage formats are advantageous particularly when access lists (e.g., white lists) for several ($10^4$-$10^6$) femto access points are aggregated or cross-linked as a result of sharing access lists.

When outcome of act 815 is positive, the access list is restored and flow is directed to act 825. Conversely, at act 825, based at least on a received directive (e.g., signaling 325) to configure access list, at least one of add an access field to the access field list or remove an access field from the access list. It should be appreciated that addition or removal of an access field in an access field can be dynamic in that memory is dynamically allocated upon addition and dynamically deallocated upon removal of an access field. Alternatively, field content(s) can be added to or removed from a static memory allocation for the access list. At act 880, it is checked if white list profile configuration is to be continued. In the affirmative outcome, flow is directed to act 875. Conversely, flow is directed to act 885 in which the access list is reformatted for storage; for instant, the updated list is aggregated with a set of access lists and recompressed. In an aspect, a format component (e.g., format component 214) can carry out the reformatting.

Figure 9:
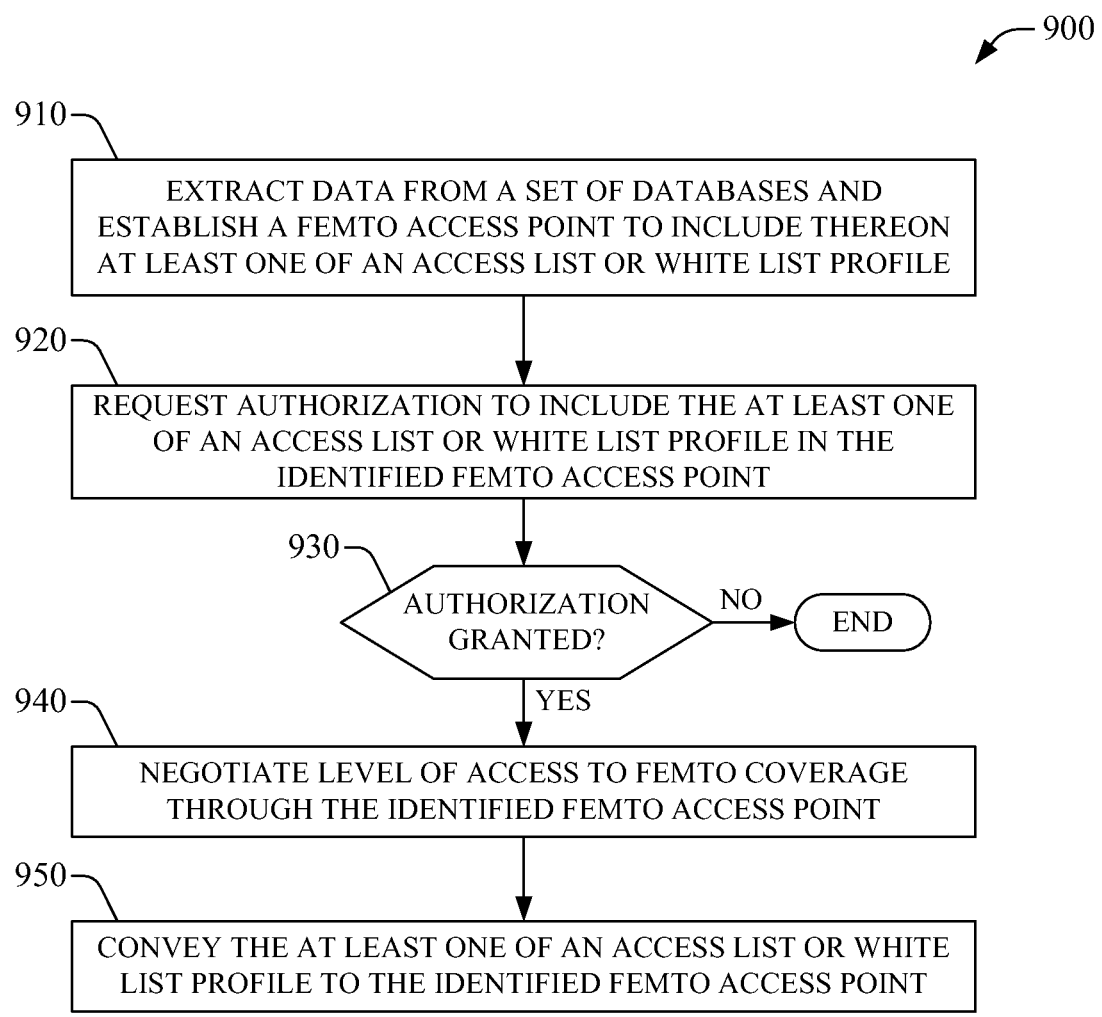
FIG. 9 is a flowchart of an example method for forwarding at least one of an access list (e.g., a white list) or a white list profile to a selected femto access point according to aspects described herein.

FIG. 9 is a flowchart of an example method 900 for forwarding at least one of an access list (e.g., a white list) or a white list profile to a selected femto access point according to aspects described herein. In an aspect, the subject example method 900 can be enacted by a component within a mobile network platform that operates a femto cell network; e.g., access list management component 210. At act 910, data is extracted form a set of databases and a femto access point to include thereon at least on of an access list of a white list profile is established. In an aspect, the set of databases can be deployed via one or more disparate networks (e.g., internet service provider network, enterprise network) linked to the mobile network platform. As an example, a database can be deployed within a local area network of an airline carrier. In an aspect, the database can be mined to determine lounge(s) with femto access points and frequent travelers that routinely utilize airport(s) in which the lounge(s) is located. Such femto access points can receive an access list (e.g., white list) and a white list profile associated therewith in order to provider a richer wireless accessibility, with premium services, for the frequent travelers.

At act 920, authorization to include the at least one of an access list or white list profile in the identified femto access point is requested. Such a request can be embodied in various communication instruments such as SMS communication, MMS communication, MBMS communication, email communication, instant message communication, or the like. The request can be conveyed to various operational layers of the network that exploits the access points; e.g., business layer(s) that can assess the request, evaluate commercial merits and feasibility, and convey approval or denial of the request. At act 930 it is evaluated if authorization is granted. In the negative case, the subject example method ends, whereas in the affirmative case a level of access to femto coverage through the identified femto access point is negotiated at act 940. In an aspect, level of coverage (e.g., QoS, type of service supported, type of devices allowed . . . ) can be negotiated for disparate segments of customer for the mobile network platform or the airline carrier. At act 950, the at least one of an access list or white list profile is conveyed to the identified femto access point; the white list profile, in an aspect, complies with negotiation in act 940.

It should be appreciated that forwarding of access control list(s) for targeted access to femto coverage has at least one advantage with respect to conventional systems that provide free-of-charge wireless services (e.g., Wi-Fi hot spots): Access to femto service is customized, through a white list profile, for each subscriber station that is entered in the access list. In the illustrative scenario of air carrier lounge(s), QoS, type of services, time span of services, or the like, can be adjusted as a function of an engagement metric among a subscriber related to the mobile device and the air carrier, e.g., number of air miles, traveler status (e.g., Elite, Gold, Platinum), or the like. In addition, customization of wireless service through the identified femto access point can be employed as a commercial driver for patrons.

Figure 10:
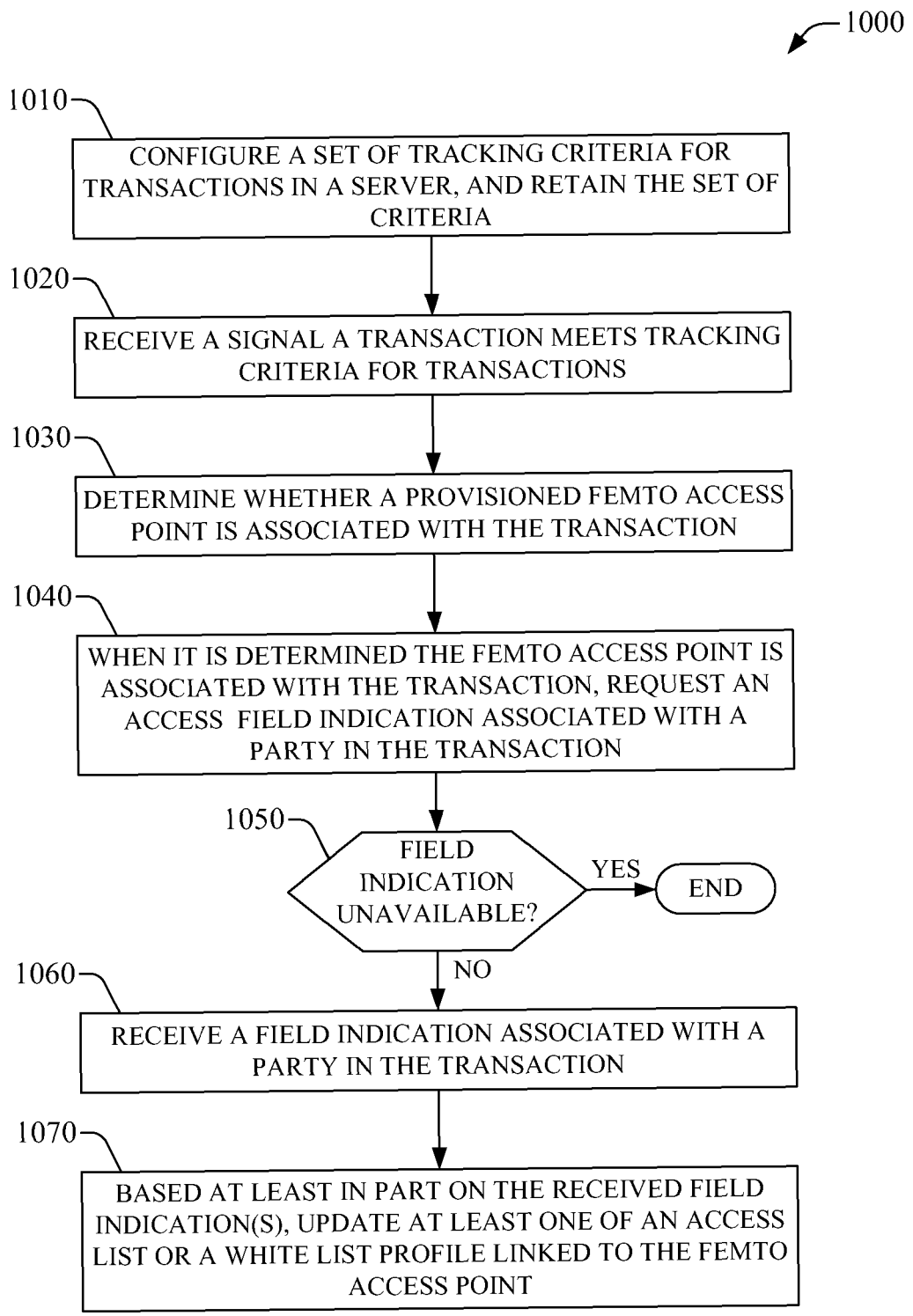
FIG. 10 presents a flowchart of an example method for updating an access list and a white list profile through generation of access fields in a server transaction according to aspects described herein.

FIG. 10 presents a flowchart of an example method 1000 for updating an access list and a white list profile through generation of access fields in a server transaction according to aspects described herein. In an aspect, the subject example method 1000 can be enacted by a component within a mobile network platform that operates a femto cell network; e.g., access list management component 210. At act 1010, a set of tracking criteria for transactions in a server are configured and retained. A server can include content servers (e.g., social network website(s), blog(s), content exchange, etc.) or ecommerce servers (e.g., online reservation system for air ticket, hotel reservation, bank transaction(s), or the like) that facilitate exchange of information. Transactions can include information dissemination, or commercial transaction(s). Transaction(s) can be secured or effected at least in part in the clear. In an aspect, tracking criteria can include identification of selected server(s), type of transaction(s), originator of the transaction, or the like. At act 1020, a signal a transaction meets tracking criteria for transaction is received. Signal can be a logic system signal, such as a multi-bit word, a set of reserved bits in control packet or frame, or the like.

At act 1030, it is determined whether a provisioned femto access point is associated with the transaction. As an example, in a hotel reservation transaction it can be determined that in a reserved room a femto access point is available. As another example, in an air travel ticket transaction, it can be determined that the selected airline carrier has access to femto coverage in an originating airport. At act 1040, when it is determined a femto access point is associated with the transaction, an access field indication associated with a party in the transaction is requested. In an aspect, an identifier number (e.g., 10-digit phone number, ESN number . . . ) for a mobile device can be provided in response to the request. Request can proceed securely as at least a part of the transaction. At act 1050, it is evaluated whether an access field indication is unavailable. In the affirmative case, the subject example method ends. Conversely, flow is directed to act 1060, in which the access field indication associated with a party n the transaction is received. At act 1070, based at least in part on the received access field indication, at least one of an access list or a white list profile linked to the femto access point is updated.

Figure 11:
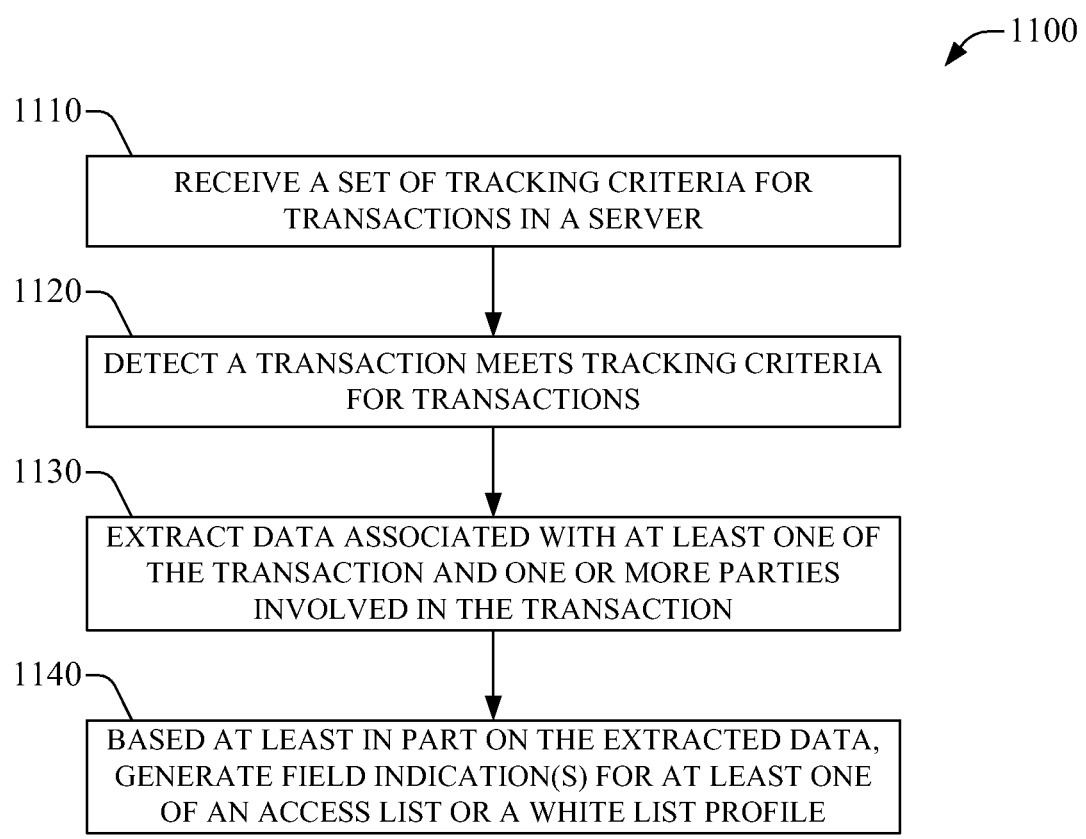
FIG. 11 presents a flowchart of an example method for providing access field indication(s) through a transaction in a server according to aspects described herein.

FIG. 11 presents a flowchart of an example method 1100 for providing access field indication(s) through a transaction in a server according to aspects described herein. A server, or component(s) therein, that facilitates the transaction can enact the subject method. At act 1110, a set of tracking criteria for transaction(s) in a server is received. In an aspect, the received set of criteria for transaction(s) is retained. At act 1120, a transaction that meets tracking criteria for transaction(s) is detected. Detection can be facilitated by a retained set of criteria for transaction(s). At act 1130, data associated with at least one of the transaction or one or more parties involved in the transaction is extracted. At act 1140, based at least in part on the extracted data, access field indication(s) for at least one of an access list or a white list profile are generated.

Figure 12:
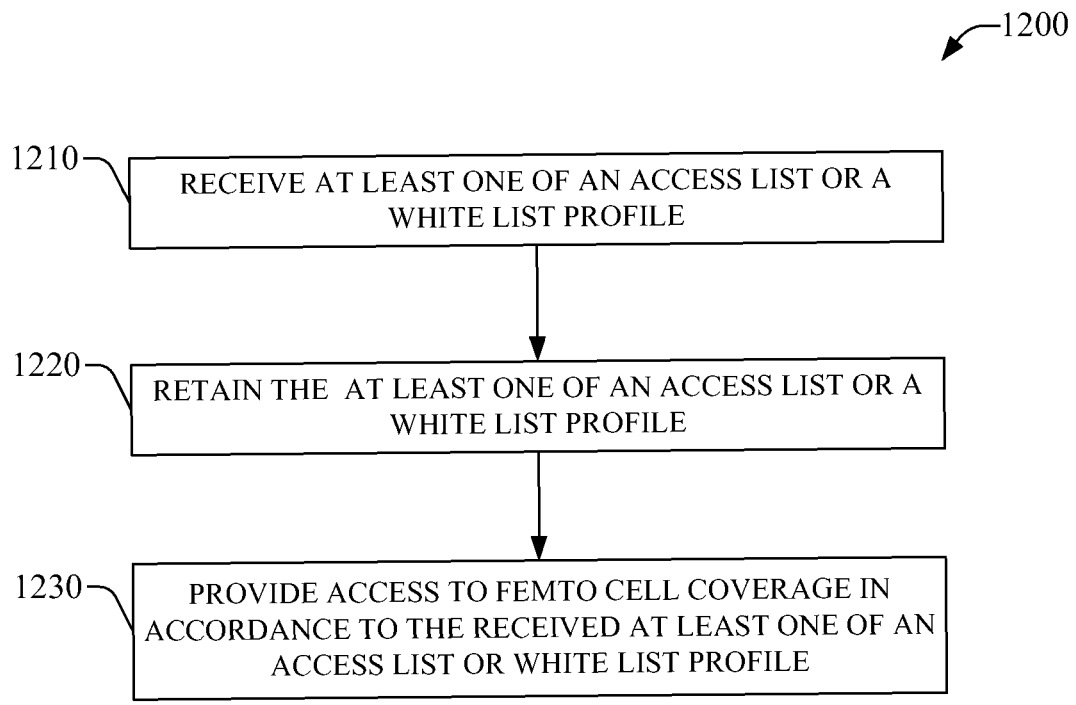
FIG. 12 presents a flowchart of an example method for utilizing an access control list (e.g., a white list or black list) or a white list profile to manage access to femto access point coverage of subscriber stations and subscribers according to aspects described herein.

FIG. 12 presents a flowchart of an example method 1200 for utilizing an access control list (e.g., a white list or black list) or a white list profile to manage access to femto access point coverage of subscriber stations and subscribers according to aspects described herein. In an aspect, the subject example method can be enacted by a femto access point (e.g., femto AP 130) that exploits the pre-populated white lists. The subject example method 1200 can be utilized with white list(s) or black list(s) and white list profile(s) configured in various manners as described in the subject specification. At act 1210, at least one of an access list or a pre-populated white list profile are received; an access list can include a white list or a black list. In another aspect, a communication platform (e.g., communication platform 357) within the femto access point receives and processes signals that carry the contents of the access list (e.g., white list(s) 343 or black list(s) 341) and a white list profile. At act 1220, the at least one of an access list (e.g., white list(s) 343 or black list(s) 341) or a white list profile (e.g., white list profile(s) 345) are retained. A memory, in the femto access AP can retain a received access list (e.g., a white list or a black list) and received white list profile. At act 1230, access to femto cell coverage is provided (e.g., granted or denied) in accordance with the received at least one of an access list (e.g., white list or black list) or white list profile.

Figure 13:
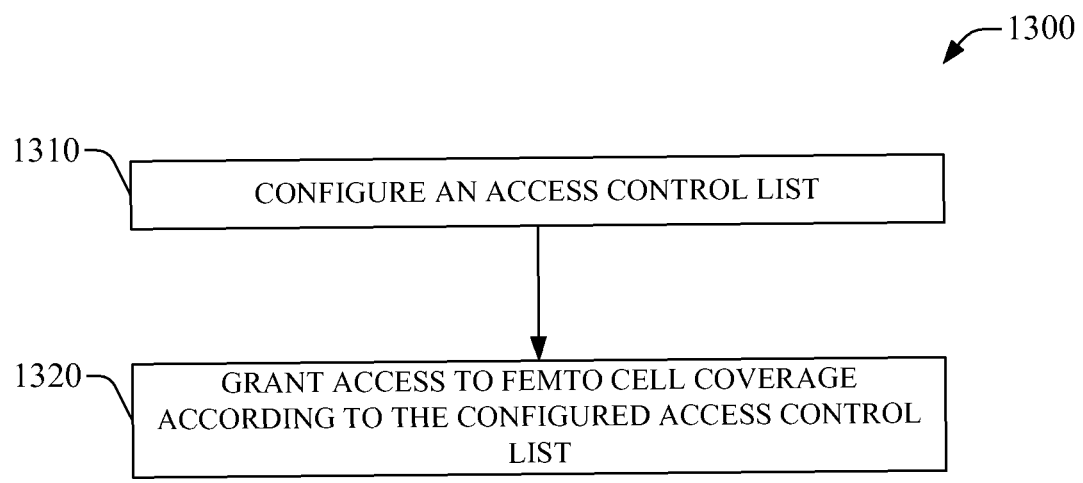
FIG. 13 presents a flowchart of an example method for managing access of subscribers and subscriber stations to femto cell coverage according to aspects described herein.

FIG. 13 presents a flowchart of an example method 1300 for managing access of subscribers and subscriber stations to femto cell coverage according to aspects described herein. At act 1310 an access control list, or white list, for a femto cell is configured. In an aspect, the subject example method can be enacted by the femto access point (e.g., femto AP 130) that exploits the pre-populated white lists. In another aspect, configuration can be performed via a networked interface, interactively or automatically based at least in part on operation conditions of the femto cell; e.g., initial provisioning, capturing of wireless devices, responding to request for access, updating extant access control lists, and so forth. At act 1320, access to femto cell coverage is granted according to the configured access control list (e.g., white list, or black list). In another aspect, the configured access control list can possess an associated profile, e.g., white list profile 234, that controls logic for utilization of the access control list, via a set of parameters that determine conditions of access, type of access, etc., as described herein.

Figure 14:
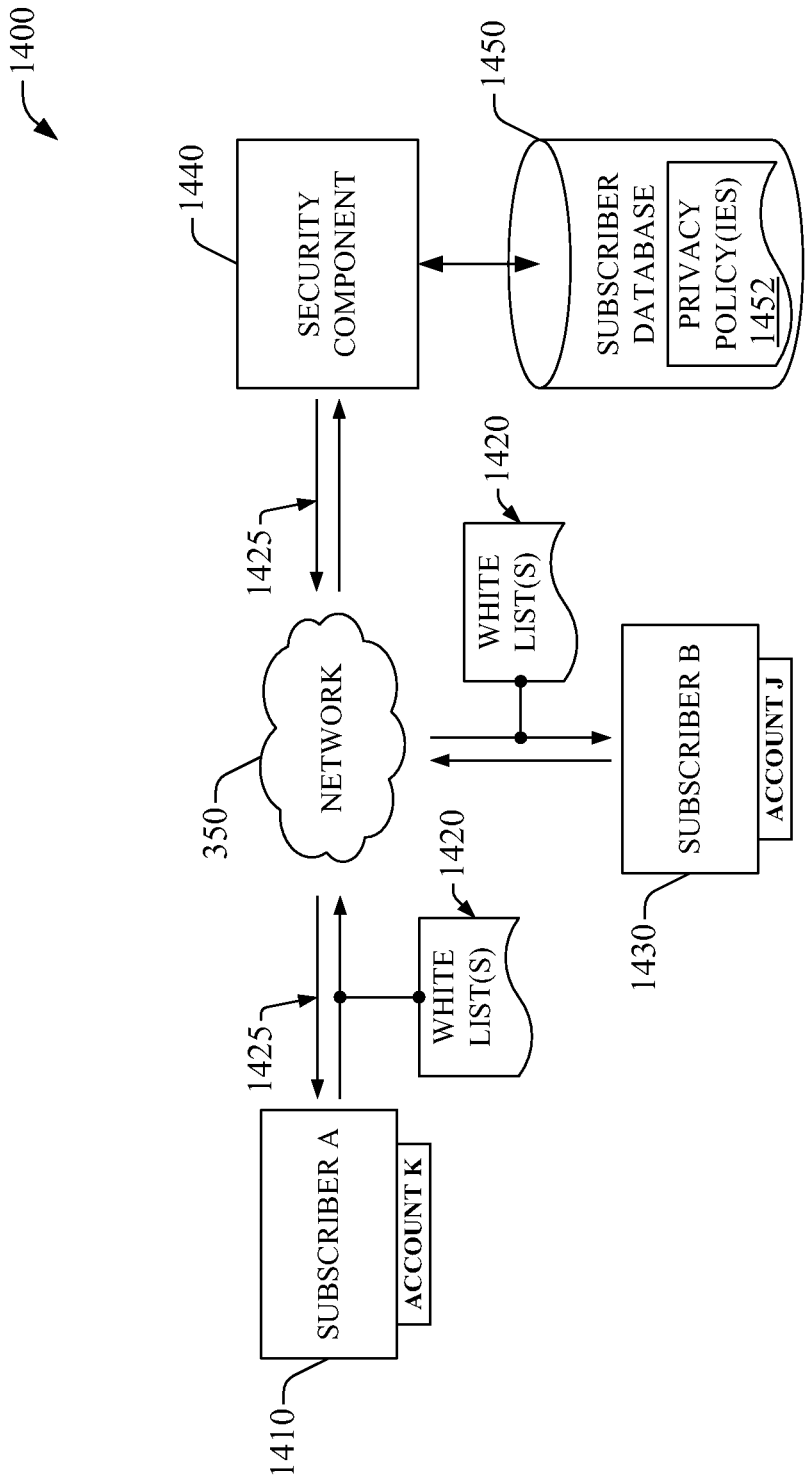
FIG. 14 is a block diagram of an example system to share access control list(s), or white list(s), in accordance with aspects described herein.

FIG. 14 is a block diagram of an example system 1400 to share access control list(s), e.g., white list(s) 1420, among subscribers of a wireless network service in order to provide straightforward access configuration to, and activation of, a femto cell (e.g., femto AP 130) among femto cell subscribers. Subscribers can belong to disparate or same service accounts with either a macro service provider or femto provide, or both. For example, subscribers that share white list(s) 1420 can pertain to a group or family associated with a single service account. In example system 1400, subscriber A 1410 who belongs to account K conveys white list(s) 1420 over network 350, via a wired or wireless link 1425, to subscriber B 1430 who belongs to account J. Subscriber A 1410 can hide or eliminate specific subscriber station numbers from white list(s) 1420 he/she/it grants to other subscribers. It should be appreciated that the granting of subscriber station numbers (e.g., MSISDNs, IMSIs . . . ), codes or tokens can substantially reduce the amount of time to configure, or set up a white list, as opposed to manually re-entering multiple (e.g., up to 50 numbers, codes or tokens) across multiple femto cells.

A security component 1440, or authorization layer, can ensure that unauthorized mobile subscriber numbers (e.g., MSISDNs, IMSIs . . . ), codes or tokens, are not provided when not approved by end users. In an aspect, security component 1440 can generate election flags that reflect whether a mobile station can be added to a white list. Such approval can be determined via a privacy policy(ies) 1452 associated with the end user, or subscriber linked to a mobile device, which can be stored in a subscriber database 1450; the privacy policy can be configured/updated through various instruments like web-based interfaces, call center, text-message center, and so on. Security component 1440 ensures privacy integrity when white list(s) 1420 are shared among subscribers of different accounts (e.g., J≠K). In an illustrative aspect, security component 1440 can solicit, or prompt, subscribers outside a "white-list share" originating account to grant the authority for their subscriber station identifier number, code or token to be shared through white list(s). To the latter end, security component 1440 can resort to various mechanisms that include, but are not limited to including, a short message service (SMS) communication, a multimedia message service (MMS) communication, instant message (IM) communication, email, voice mail, web pop up, and so on. Alternatively, or in addition, security component 1440 can mitigate security mechanism(s) complexity through validation via subscriber account information such as election (e.g., opt-in/opt-out) flags (e.g., stored in subscriber database 1450) in order to grant automatic access to white list(s) within groups or families underneath a single service account, without additional security verification.

Figure 15:
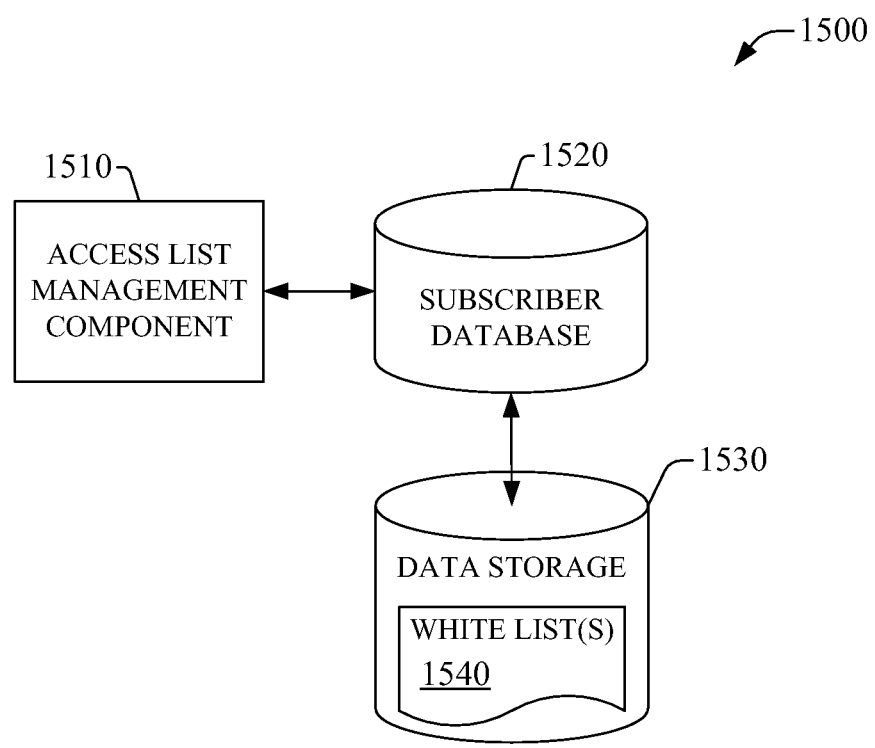
FIG. 15 is a block diagram of an example system that manages access control lists, or white lists, in accordance with aspects described herein.

FIG. 15 is a block diagram of an example system 1500 that manages access control lists (e.g., white lists or black lists) in accordance with aspects described herein. White list management component 1510, via for example data mining component 351, can access a subscriber database 1520 which can be maintained by a service operator for femto and macro networks, and a data storage 1530 that retains a set of white lists 1540 associated with served subscribers, to associate whitelisted subscribers across disparate access control lists, or white lists. It should be appreciated that component 1510 can operate in the same manner as access list management component 210. It should further be appreciated that data storage 1530 can be associated with various network platforms (e.g., service network(s), enterprise network(s), local area network(s) . . . ) linked to a mobile network platform operated by the service provider. Such association can lead to genesis of white-list trees. In an aspect, access list management component 1520 via, for example, a format component (e.g., format component 214) can implement mechanisms to mitigate exponential data growth and efficient storage of white-list trees like data-compression (e.g., wavelet, efficient tree representation, or the like), distributed data warehouses, and so forth. In another aspect, access list management component 1520 can deploy a white-list tree in accordance to the following illustrative, non-limiting scenario. (i) User 1 adds User 2 to his/her white list. (ii) User 2 adds User 3 to his/her white list. (iii) User 1 and User 3 can be associated through white lists. (iv) User 1 and User 3 can match User 4 extant on each other's white lists. (v) User 1 and User 3 can associate User 5 that is on User 4's white list. In an aspect, access list management component 1510 effects associations and manages generated white-list tree(s). It should be appreciated that substantially any association, hierarchical or non-hierarchical, or deployment of white lists (e.g., white list(s) 1540) can be implemented by access list management component 1510 through information stored in subscriber database 1520 and data storage 1530. An illustrative, non-limiting, advantage of structured, hierarchical generation of white lists to subscribers (e.g., subscriber A 1110) is that more subscribers can have access to femto cells to gain wireless coverage enhancement, or have access to added value through unlimited usage on any femto cell or unique services available via a set of femto cells.

In addition, example system 1500 can track subscriber station identifier numbers (e.g., MSISDNs, IMSIs), codes or tokens, associated with white list(s) on record with a femto service provider. White list management component 1510 can validate white list(s) 1540, stored in data storage 1530, against current accounts and associated subscriber station identifier numbers (e.g., MSISDNs, IMSIs), codes, or tokens, for a service provider. In particular, when a subscriber (e.g., subscriber A 1410), or end user, cancels an account with service provider, white list(s) 1540 can be updated according to information retrieved from subscriber database 1520, which is updated as a result of the cancelled subscription, or substantially any other database available to a service provider that contains information on service subscribers. In addition, when an end user changes their mobile or subscriber station number, code or token, (e.g., after relocation to a new area code, or the like) substantially all white list(s) 1540 that the mobile or subscriber station number, code or token is associated with can automatically be updated by white list management component 1510.

An illustrative advantage of such automatic update of white list(s) 1540 is ease of use for end users to maintain current white list(s) 1540 without a need to keep track of each subscriber station number, code, or token associated with the white list(s) 1540. In addition, updated white list(s) 1540 maintains the value proposition of the femto cells for end users and service operator by a seamless move of traffic off of the macro network (e.g., a WAN) to femto network(s).

Figure 16:
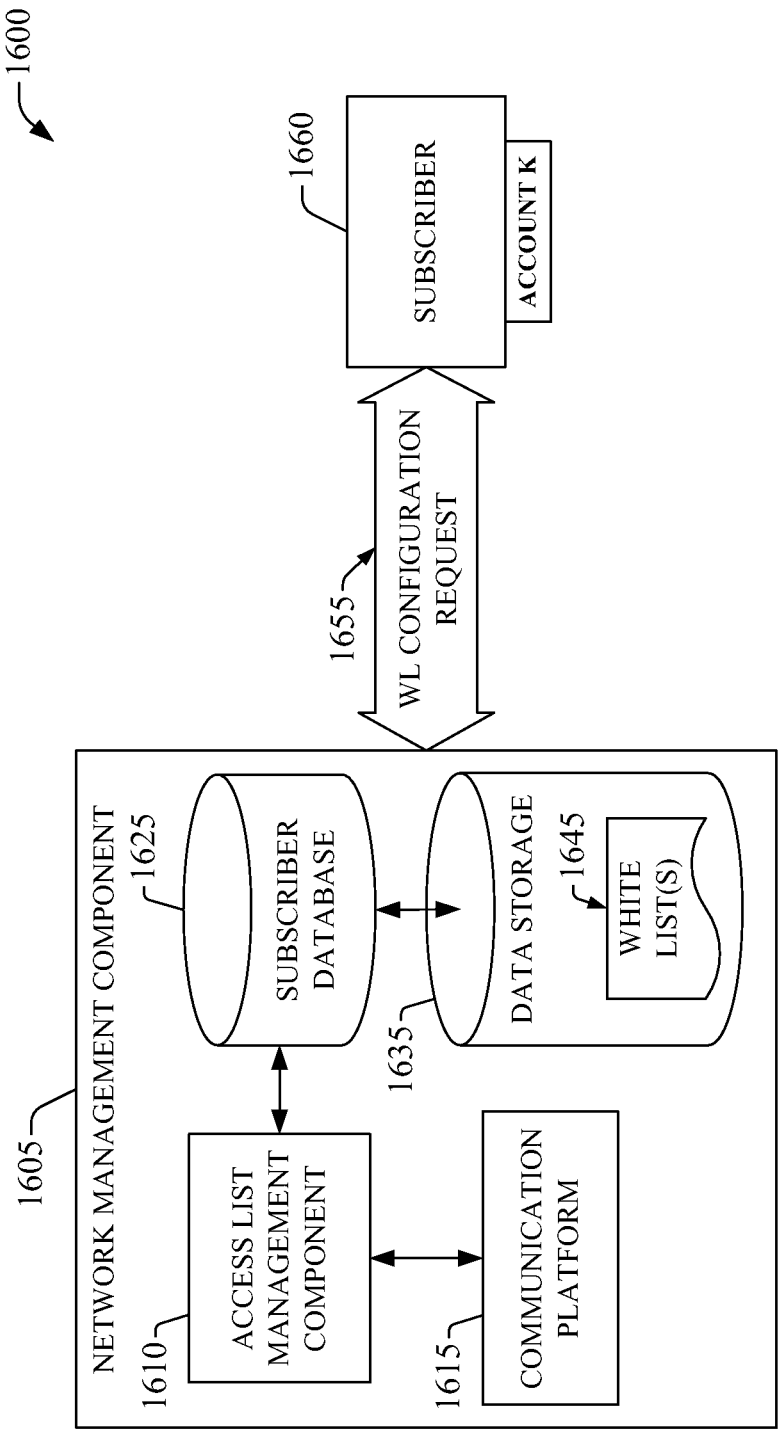
FIG. 16 is a block diagram of an example system that facilitates addition of subscriber(s)/subscriber station(s) to one or more white lists in accordance with aspects described in the subject specification.

FIG. 16 is a block diagram of an example system 1600 that facilitates addition of subscriber(s)/subscriber station(s) to one or more white list(s) 1645 in accordance with aspects described herein. In example system 1600, a network management component 1610 (e.g., a provisioning server) includes an access list management component 1610 which is coupled to a subscriber database 1625, a data storage 1635 and a communication platform 1615. Access list management component 1610 operates in the same manner as access management component 1610. The access list management component 1610 can data-mine, e.g., through a data mining component 216, subscriber database 1625 and white list(s) 1645, which resides in data storage 1635, to drive addition of new subscribers who have opted in to be included in white list(s) to a white list to request reciprocal adding. In an aspect, when a subscriber 1660 in account K is identified for reciprocal addition, at a time the subscriber 1660 configures his/her femto AP, a white list (WL) configuration request 1655 is conveyed (e.g., via a wired or wireless link through communication platform 1615) to the subscriber. Such WL configuration request 1655 indicates that a disparate subscriber (e.g., subscriber B 1430) has subscriber 1660 white-listed and prompts subscriber 1660 to include in his/her white list the disparate subscriber. An illustrative scenario is the following: User 1 adds User 2 to his/her white list. When User 2 configures/activates his/her femto cell, a setup process (implemented, for example, through a web-based online GUI) will prompt User 2 to add User 1. It is to be noted that access list management component 1210 can exploit information in subscriber database 1625 and data storage 1635 to inform User 2 of substantially all subscriber station numbers, codes or tokens that he/she can add automatically on a reciprocity basis; namely, User 2 can be prompted to add in white list(s) those subscribers that have previously added him/her to their with list(s). White list configuration request 1655 can be effected through various interfaces like an online GUI, a real time prompt/alert delivered via SMS, MMS, email, instant message, USSD communication, and so forth.

Figure 17:
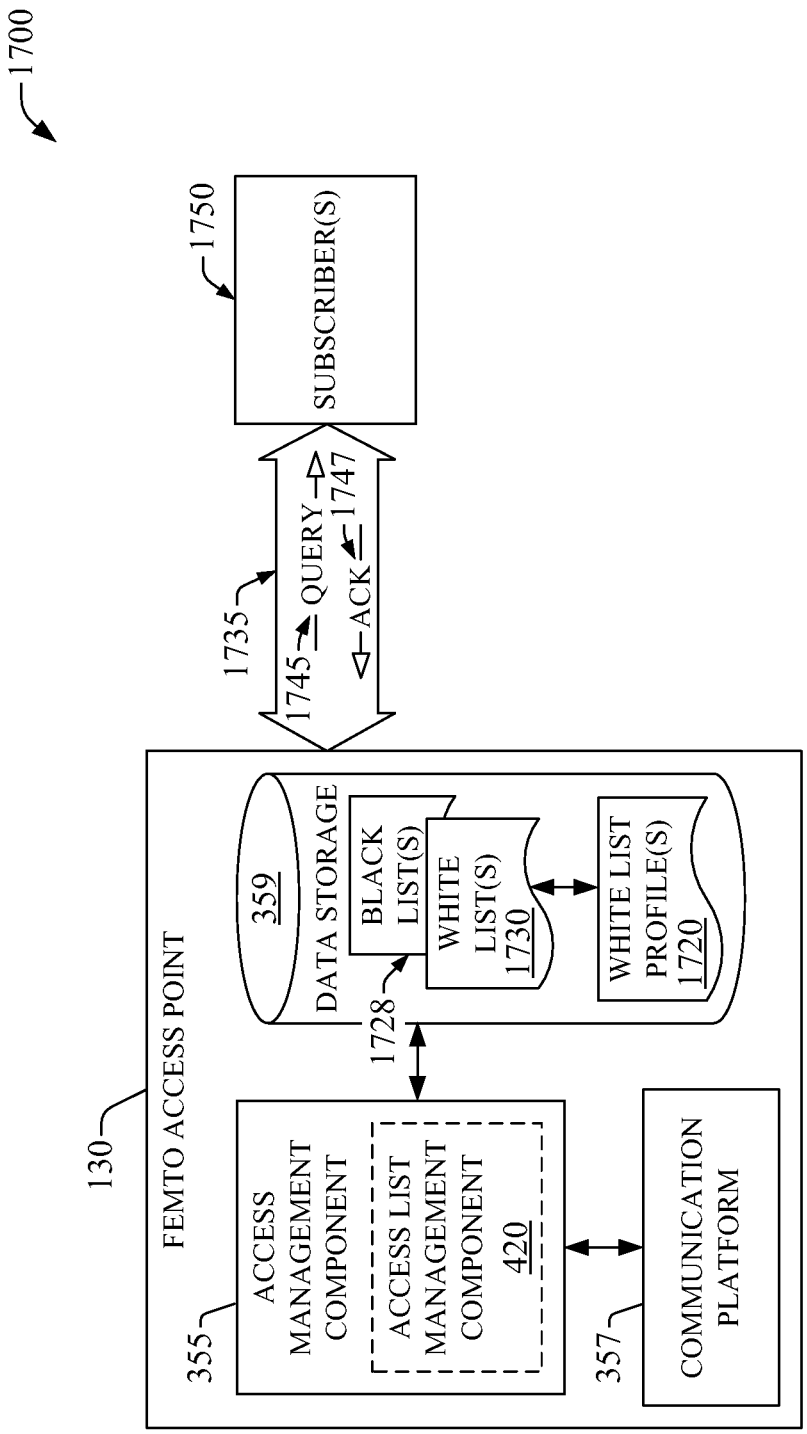
FIG. 17 is a block diagram of an example system that manages a defined logic of how content(s) in access control list(s), e.g., white list(s) or black list(s), is maintained on a white list profile retained in a database in accordance with aspects described herein.

FIG. 17 is a block diagram of an example system 1700 that manages a defined logic of how content(s) (e.g., MSISDNs, IMSIs, IMEIs . . . ) in access control list(s), e.g., white list(s) or black list(s), are maintained on a white list profile retained in a database, which can be embodied in data storage 245. Access management component 355, which can comprise an access list (e.g., white list) management component 420, can develop white list profile(s) 1720 that applies logic and parameters that control, or manage, content (e.g., attribute fields) in white list(s) 1730 such as subscriber station numbers (e.g., MSISDNs, IMSIs, IMEIs . . . ), codes, or tokens. White list profile(s) 1720 and white list(s) 1730 can be stored in data storage 359; it should be appreciated that while data storage 359 is illustrated to reside within femto access point 130, such storage can reside in a network management component (e.g., component 1605), or can be functionally coupled thereof.

As described above in connection with example system 200, white list profile(s) 1720 parameters that control utilization logic of white list(s) 1730 content include, without being limited to including: (i) temporary access parameters, e.g., full access for a specific time interval such as days or hours; (ii) parameters that establish access only within a window of time in a day (voice and data allowed from 9:00 a-6:00 p, or voice allowed after 9:00 p which can facilitate billing schemes already established by an operator/service provider); (iii) parameters for access to specific applications such as scheduler, calendar(s), news streaming, authoring tools, gaming, video and music, etc; (iv) parameters for access to femto AP 130 coverage with specific QoS profile(s), band width, allocated power for communication, or the like.

In another aspect, as indicate above, logic within white list profile(s) 1720 can implement parameters to determine how long access to femto coverage is granted. For instance, when a timer associated with temporary access expires, a query 1745 can be triggered or conveyed (e.g., through a wired or wireless link 1735) to either a subscriber that operates a device associated with the managed identifier (e.g., MSISDN, IMSI, IMEI) in order to prompt or request renewed access, or to a subscriber that operates femto access point 130. The message request, e.g., query 1745, can prompt the subscriber that owns femto AP 130 whether an extension is to be granted or not. When a request is not granted by a subscriber that operates femto AP 130 or there is no reply, e.g., acknowledgement 1745, from the subscriber owner, access to femto coverage expires and the identifier (e.g., MSISDN, or substantially any identifier code or token) linked to an identified mobile device is deleted from a corresponding white list(s) 1730 within data storage 359. It should be appreciated that the deletion can be "soft," e.g., the identifier is flagged as inactive, or "hard," wherein the identifier is deleted and a field or slot in a white list(s) 1420 is made available. Conversely, a positive response, e.g., acknowledgement (ACK) 1747, from subscriber owner can allow access to continue based on either parameters extant in white list profile(s) 1420, or newly defined or negotiated access logic parameters. It is to be noted that query 1445 can be conveyed via an online GUI, an email message, a SMS message, MMS message, a voice mail, a web prompt, and the like.

Figure 18:
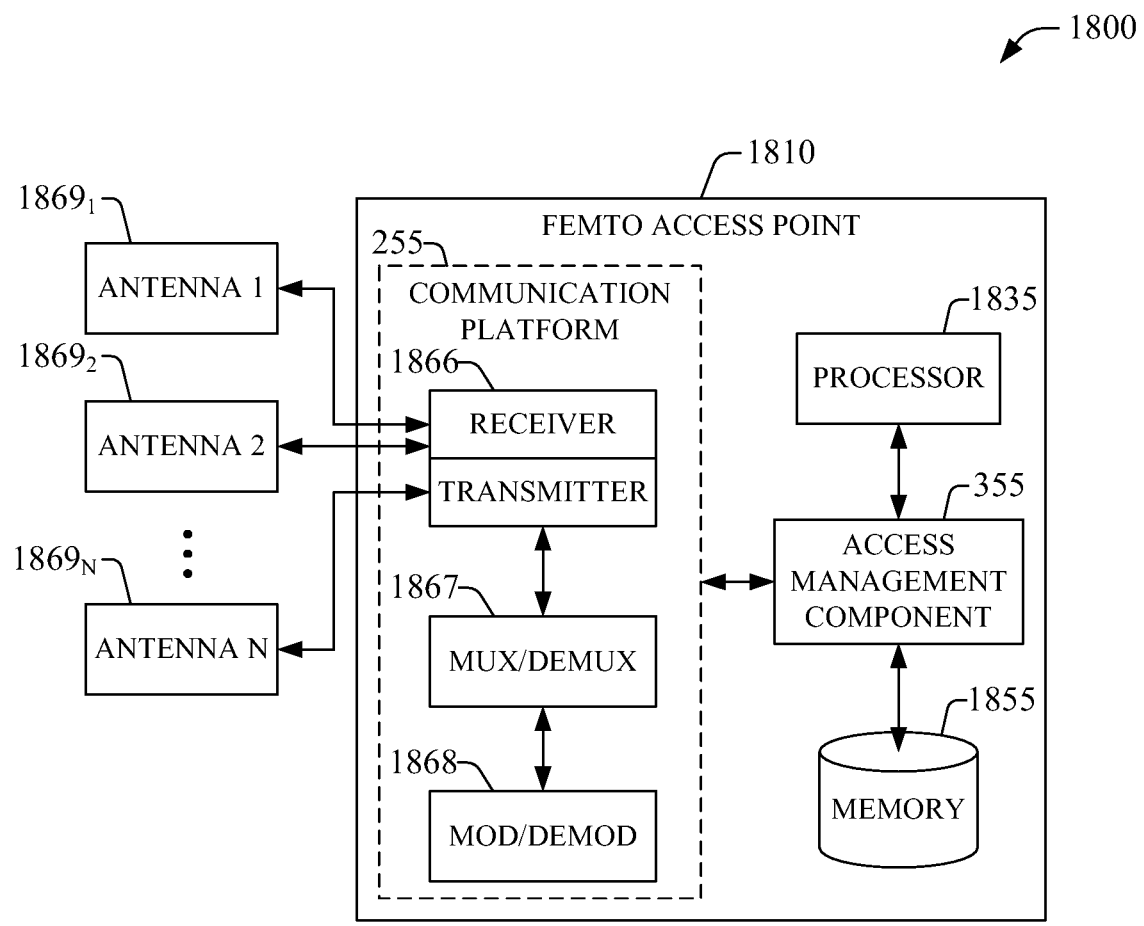
FIG. 18 is a block diagram of an example femto access point that operates in accordance with aspects disclosed in the subject specification.
Figure 19:
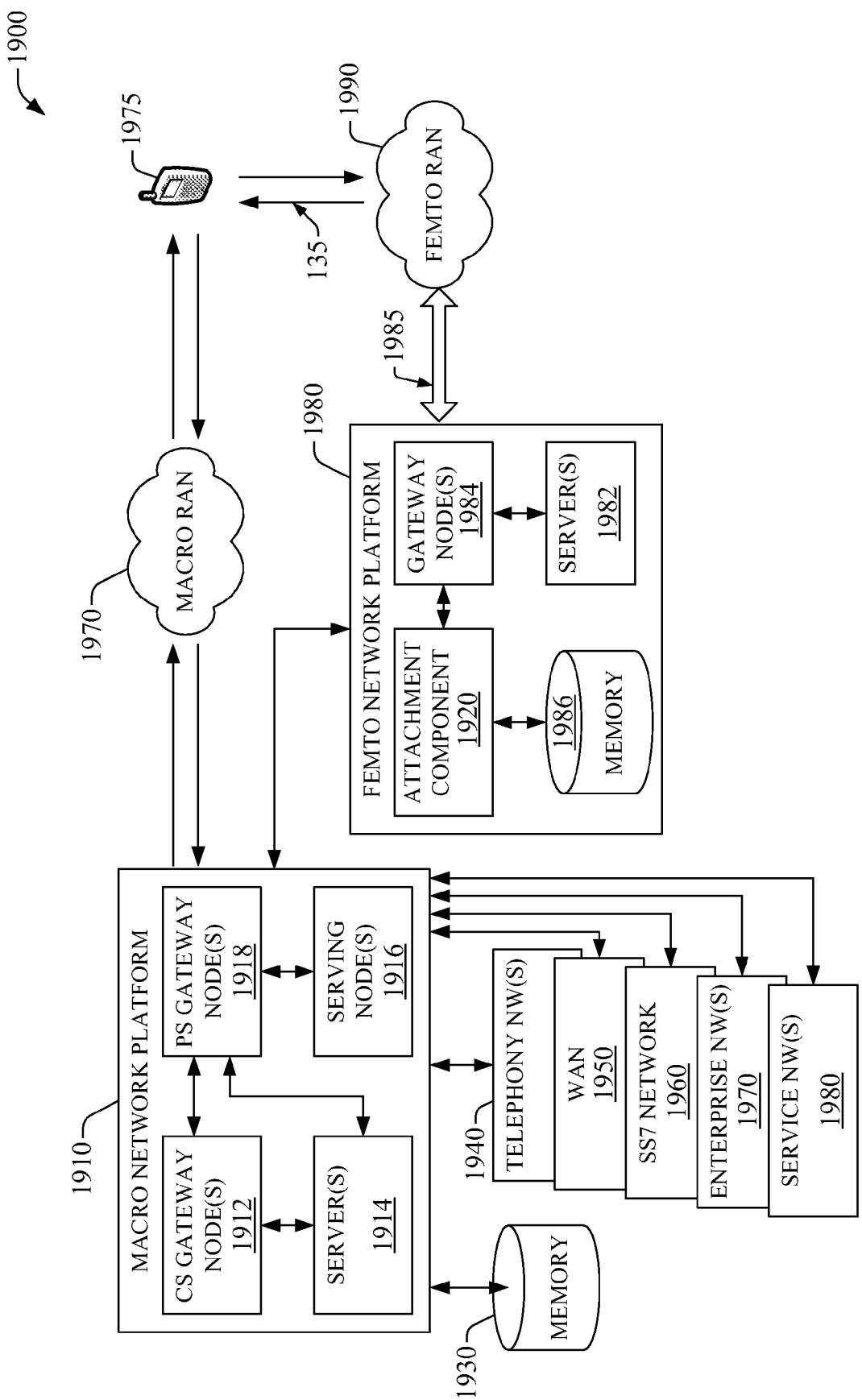
FIG. 19 illustrates example macro and femto wireless network environments that can enable and implement various aspects of the subject innovation, and can exploit femto APs that operate according to the various aspects.

To provide further context for various aspects or features of the subject specification, in system in which aspects or features of the subject innovation can be exploited, FIG. 18 illustrates a block diagram of an example embodiment 1800 of a femto access point that can enable and exploit and manage femto coverage via access control list(s), or white list(s), in accordance with aspects described herein. In addition, FIG. 19 illustrates a block diagram of an illustrative telecommunication network 1900 that can enable or implement, and exploit features and aspects described herein. Those skilled in the art will recognize that the specification also be implemented through program modules stored in a memory and executed by a processor, and/or other combination of hardware and software.

With respect to FIG. 18, in embodiment 1800, femto AP 1810 can receive and transmit signal(s) from and to wireless devices like macro and femto access points, access terminals, wireless ports and routers, and the like, through a set of antennas $1869_1$-$1769_N$. It should be appreciated that while antennas $1869_1$-$1869_N$ are a part of communication platform 255, which comprises electronic components and associated circuitry that provides for processing and manipulation of received signal(s) and signal(s) to be transmitted. In an aspect, communication platform 255 includes a receiver/transmitter 1866 that can convert signal from analog to digital upon reception, and from digital to analog upon transmission. In addition, receiver/transmitter 1866 can divide a single data stream into multiple, parallel data streams, or perform the reciprocal operation. Coupled to receiver/transmitter 1866 is a multiplexer/demultiplexer 1867 that facilitates manipulation of signal in time and frequency space. Electronic component 1867 can multiplex information (data/traffic and control/signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 1867 can scramble and spread information (e.g., codes) according to substantially any code known in the art; e.g., Hadamard-Walsh codes, Baker codes, Kasami codes, polyphase codes, and so on. A modulator/demodulator 1868 is also a part of operational group 1825, and can modulate information according to multiple modulation techniques, such as frequency modulation, amplitude modulation (e.g., M-ary quadrature amplitude modulation (QAM), with M a positive integer), phase-shift keying (PSK), and the like.

Femto access point 1810 also includes a processor 1835 configured to confer functionality, at least partially, to substantially any electronic component in the femto access point 1810. In particular, processor 1835 can facilitate access management component 355 to supply fixed differentiated QoS in accordance to aspects disclosed herein. In addition, processor 1835 can facilitate operations on data (e.g., symbols, bits, or chips) for multiplexing/demultiplexing, such as effecting direct and inverse fast Fourier transforms, selection of modulation rates, selection of data packet formats, inter-packet times, etc. A memory 1855 can store data structures, code instructions, system or device information like policies and specifications, code sequences for scrambling, spreading and pilot transmission, floor plan configuration, access point deployment and frequency plans, scheduling policies, and so on.

In embodiment 1800, processor 1834 is coupled to the memory 1855 in order to store and retrieve information necessary to operate and/or confer functionality to communication platform 255, access management component 235, and other operational aspects of femto access point 1810.

With respect to FIG. 19, wireless communication environment 1900 includes two wireless network platforms: (i) A macro network platform 1910 which serves, or facilitates communication with user equipment 1975 (e.g., mobile $120_A$) via a macro radio access network (RAN) 1970. It should be appreciated that in cellular wireless technologies (e.g., 3GPP UMTS, High-Speed Packet Access (HSPA), 3GPP LTE, 3GPP2 UMB), macro network platform 1910 is embodied in a Core Network. (ii) A femto network platform 1980, which can provide communication with UE 1975 through a femto RAN 1990, which is linked to the femto network platform 1980 via backhaul pipe(s) 1985 (e.g., backhaul link(s) 140). It should be appreciated that macro network platform 1910 typically hands off UE 1975 to femto network platform 1910 when UE 1975 attaches (e.g., through macro-to-femto handover) to femto RAN 1990, which includes a set of deployed femto APs (e.g., femto AP 130) that can operate in accordance with aspects described herein.

It is noted that RAN includes base station(s), or access point(s), and its associated electronic circuitry and deployment site(s), in addition to a wireless radio link operated in accordance with the base station(s). Accordingly, macro RAN 1970 can comprise various coverage cells like cell 105, while femto RAN 1990 can comprise multiple femto cell access points such as femto AP 130. Deployment density in femto RAN 1890 is substantially higher than in macro RAN 1970.

Generally, both macro and femto network platforms 1910 and 1980 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject innovation, macro network platform 1910 includes CS gateway node(s) 1812 which can interface CS traffic received from legacy networks like telephony network(s) 1940 (e.g., public switched telephone network (PSTN), or public land mobile network (PLMN)) or a SS7 network 1960. Circuit switched gateway 1912 can authorize and authenticate traffic (e.g., voice) arising from such networks. Additionally, CS gateway 1912 can access mobility, or roaming, data generated through SS7 network 1960; for instance, mobility data stored in a VLR, which can reside in memory 1930. Moreover, CS gateway node(s) 1912 interfaces CS-based traffic and signaling and gateway node(s) 1918. As an example, in a 3GPP UMTS network, PS gateway node(s) 1918 can be embodied in gateway GPRS support node(s) (GGSN).

In addition to receiving and processing CS-switched traffic and signaling, PS gateway node(s) 1818 can authorize and authenticate PS-based data sessions with served (e.g., through macro RAN) wireless devices. Data sessions can include traffic exchange with networks external to the macro network platform 1910, like wide area network(s) (WANs) 1850, enterprise networks (NW(s)) 1870 (e.g., enhanced 911), or service NW(s) 1880 like IP multimedia subsystem (IMS); it should be appreciated that local area network(s) (LANs), which may be a part of enterprise NW(s), can also be interfaced with macro network platform 1910 through PS gateway node(s) 1818. Packet-switched gateway node(s) 1918 generates packet data contexts when a data session is established. To that end, in an aspect, PS gateway node(s) 1918 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 1914. It is to be noted that in 3GPP UMTS network(s), PS gateway node(s) 1918 (e.g., GGSN) and tunnel interface (e.g., TTG) comprise a packet data gateway (PDG).

Macro network platform 1910 also includes serving node(s) 1916 that conveys the various packetized flows of information, or data streams, received through PS gateway node(s) 1918. As an example, in a 3GPP UMTS network, serving node(s) can be embodied in serving GPRS support node(s) (SGSN).

As indicated above, server(s) 1914 in macro network platform 1910 can execute numerous applications (e.g., location services, online gaming, wireless banking, wireless device management . . . ) that generate multiple disparate packetized data streams or flows, and manage (e.g., schedule, queue, format . . . ) such flows. In addition, in an aspect, server(s) 1914 can embody, at least in part, access list management component 210. Such application(s), for example can include add-on features to standard services provided by macro network platform 1910. Data streams can be conveyed to PS gateway node(s) 1918 for authorization/authentication and initiation of a data session, and to serving node(s) 1916 for communication thereafter. Server(s) 1914 can also effect security (e.g., implement one or more firewalls) of macro network platform 1910 to ensure network's operation and data integrity in addition to authorization and authentication procedures that CS gateway node(s) 1912 and PS gateway node(s) 1918 can enact. Moreover, server(s) 1914 can provision services from external network(s), e.g., WAN 1950, or Global Positioning System (GPS) network(s), which can be a part of enterprise NW(s) 1980. It is to be noted that server(s) 1914 can include one or more processor configured to confer at least in part the functionality of macro network platform 1910. To that end, the one or more processor can execute code instructions stored in memory 1930, for example.

In example wireless environment 1900, memory 1930 stores information related to operation of macro network platform 1910. Information can include business data associated with subscribers; market plans and strategies, e.g., promotional campaigns, business partnerships; operational data for mobile devices served through macro network platform; service and privacy policies; end-user service logs for law enforcement; and so forth. Memory 1930 can also store information from at least one of telephony network(s) 1940, WAN 1950, SS7 network 1960, enterprise NW(s) 1970, or service NW(s) 1980.

Regarding femto network platform 1980, it includes a femto gateway node(s) 1984, which have substantially the same functionality as PS gateway node(s) 1918. Additionally, femto gateway node(s) 1984 can also include substantially all functionality of serving node(s) 1916. Disparate gateway node(s) 1984 can control or operate disparate sets of deployed femto APs, which can be a part of femto RAN 1990. In an aspect of the subject innovation, femto gateway node(s) 1984 can aggregate operational data received from deployed femto APs. Moreover, femto gateway node(s) 1984, can convey received attachment signaling to attachment component 1920. It should be appreciated that while attachment component is illustrated as external to gateway node(s) 1984, attachment component 1920 can be an integral part of gateway node(s) 1984.

Attachment component 1920 can facilitate macro-to-femto and femto-to-macro handover with attachment to a femto AP (e.g., femto AP 130) dictated in accordance to a white list (e.g., white list(s) 220) and/or a white list profile (e.g., white list profile(s) 222). In an aspect, attachment component 1920 can include a determination of whether a white list resides within femto AP and whether a mobile station that is attempting attachment is whitelisted as described in the subject innovation. It is noted, in an aspect, that when a whitelisted mobile station is allowed to attach to the femto AP, attachment component 1920 can establish femto service in accordance with privileges, or access logic, configured in a white list profile (e.g., white list profile(s) 222).

Memory 1986 can retain additional information relevant to operation of the various components of femto network platform 1980. For example operational information that can be stored in memory 1986 can comprise, but is not limited to, subscriber intelligence; contracted services; maintenance and service records; femto cell configuration (e.g., devices served through femto RAN 1990; authorized subscribers associated with one or more deployed femto APs); service policies and specifications; privacy policies; add-on features; so forth.

Server(s) 1982 have substantially the same functionality as described in connection with server(s) 1914. In an aspect, server(s) 1982 can execute multiple application(s) that provide service (e.g., voice and data) to wireless devices served through femto RAN 1990. Server(s) 1982 can also provide security features to femto network platform. In addition, server(s) 1982 can manage (e.g., schedule, queue, format . . . ) substantially all packetized flows (e.g., IP-based, frame relay-based, ATM-based) it generates in addition to data received from macro network platform 1910. Furthermore, server(s) 1982 can effect provisioning of femto cell service, and effect operations and maintenance. It is to be noted that server(s) 1982 can embody provisioning server 345, and can populate white list(s) and white list profile(s) in accordance with aspects described herein. It is to be noted that server(s) 1982 can include one or more processors configured to provide at least in part the functionality of femto network platform 1980. To that end, the one or more processors can execute code instructions stored in memory 1986, for example.

Various aspects or features described herein may be implemented as a method, apparatus, or article of manufacture using standard programming and/or engineering techniques. Implementation(s) that include software or firmware can be implemented at least in part through program modules stored in a memory and executed by a processor. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disc (CD), digital versatile disc (DVD), blu-ray disc (BD) . . . ), smart cards, and flash memory devices (e.g., card, stick, key drive . . . ).

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," data storage," "database," and substantially any other information storage component relevant to operation and functionality of a component, refer to "memory components," or entities embodied in a "memory" or components comprising the memory. For example, information relevant to operation of various components described in the disclosed subject matter, and that can be stored in a memory, can comprise, but is not limited to comprising, subscriber information; femto cell configuration (e.g., devices served by a femto AP; access control lists, or white lists) or service policies and specifications; privacy policies; and so forth. It will be appreciated that the memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ES-DRAM), Synchlink DRAM (SLDRAM), and direct Rambus RAM (DRRAM). Additionally, the disclosed memory components of systems or methods herein are intended to comprise, without being limited to comprising, these and any other suitable types of memory.

What has been described above includes examples of systems and methods that provide advantages of the subject innovation. It is, of course, not possible to describe every conceivable combination of components or methodologies for purposes of describing the claimed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A method, comprising:
   receiving, by a system comprising a processor, access field indication data, comprising identifier data indicative of an identifier of a mobile device, for inclusion in an access control data structure associated with a femtocell device, wherein the access control data structure is employed to control access to the femtocell device;
   comparing, by the system, the identifier data with information associated with the mobile device that is received from a subscriber data store within a macro network; and
   in response to determining, based on the comparing, that the identifier is an active identifier, updating, by the system, the access control data structure with the access field indication data.

2. The method of claim 1, wherein the receiving comprises receiving data that specifies a type of service allowed to be employed by the mobile device, in response to the mobile device being determined to be coupled to the femtocell device.

3. The method of claim 1, wherein the receiving comprises receiving data that specifies a time period during which the mobile device is authorized to access the femtocell device.

4. The method of claim 1, further comprising:
   in response to determining, based on the comparing, that the identifier is not the active identifier,
     receiving, by the system, active identifier data indicative of the active identifier, and
     updating, by the system, the access control data structure with the active identifier data.

5. The method of claim 1, wherein the receiving comprises receiving data that specifies a priority associated with services provided to the mobile device via the femtocell device.

6. The method of claim 1, wherein the receiving comprises receiving the access field indication data via a text message.

7. The method of claim 1, further comprising:
   determining, by the system, commercial standing data indicative of a commercial standing of the mobile device, wherein the updating comprises updating the access control data structure, in response to the commercial standing data being determined to satisfy a commercial standing criterion.

8. The method of claim 1, wherein the receiving comprises receiving the access field indication data via a packet header data of a communication message.

9. The method of claim 1, wherein the receiving comprises receiving data that specifies a wireless technology employed by the mobile device for communication.

10. The method of claim 1, further comprising:
subsequent to the updating, determining, by the system, a change in the identifier data; and
based on the change, updating the access control data structure.

11. The method of claim 1, further comprising:
receiving, by the system, authorization data indicative of an authorization to store the access control data structure from a subscriber device associated with the femtocell device; and
negotiating, by the system, a level of access to femto coverage provided via through the femtocell device, in response to the receiving the authorization data.

12. The method of claim 1, further comprising:
facilitating, by the system, a transmission of the access control data structure to the femtocell device.

13. The method of claim 1, wherein the access field indication is a first access field indication, and the method further comprises:
configuring, by the system, a tracking criterion for a transaction in a server of the macro network;
receiving, by the system, signaling data indicating that the transaction is determined to satisfy the tracking criterion;
determining, by the system, that the femtocell device is associated with the transaction; and
requesting, by the system, second access field indication data associated with a communication device associated with the transaction, in response to the determining that the femtocell device is associated with the transaction.

14. The method of claim 13, further comprising:
receiving, by the system, the second access field indication data; and
based on the second access field indication data, modifying, by the system, the access control data structure linked to the femtocell device.

15. The method of claim 1, wherein the receiving comprises receiving the access field indication data that specifies a radio frequency band employed by the mobile device for communication.

16. A system, comprising:
a memory to store instructions; and
a processor, coupled to the memory, that facilitates execution of the instructions to perform operations, comprising:
receiving an access field indication data associated with an access control data structure relating to a femtocell device, wherein the access control data structure is employed to control access to the femtocell device and the access field indication data comprises identifier data indicative of an identifier of a mobile device that is authorized to access the femtocell device;
receiving information associated with the mobile device from a subscriber data store of a macro network, prior to entering the access field indication data identifier into the access control data structure; and
in response to a determination, based on the information, that the identifier is an active identifier of the mobile device, adding the access field indication data to the access control data structure.

17. The system of claim 16, wherein the access field indication data is received from a user equipment associated with the femtocell device via a text message.

18. The system of claim 16, wherein the access field indication data further comprises data that specifies a radio frequency band employed by the mobile device for communication.

19. The system of claim 16, wherein the operations further comprise:
in response to determining, based on the information, that the identifier is not the active identifier, receiving, active identifier data indicative of the active identifier and adding the active identifier data to the access control data structure.

20. The system of claim 16, wherein the operations further comprise:
determining that the access field indication data is authorized for inclusion within the access control data structure, based on status data of an election flag associated with the mobile device.

21. The system of claim 16, wherein the operations further comprise:
facilitating formatting of the access control data structure in accordance with a markup language format.

22. The system of claim 21, wherein the formatting comprises indexing the access control data structure.

23. The system of claim 16, wherein the access field indication data further comprises data that specifies a wireless technology employed by the mobile device for communication.

24. The system of claim 16, wherein the access field indication data is received from a user equipment associated with the femtocell device via a packet header of a communication message.

25. The system of claim 16, wherein the operations further comprise:
monitoring a service subscribed by the mobile device; and
updating the access control data structure in response to determining a change in the service.

26. The system of claim 16, wherein the operations further comprise:
subsequent to the adding, determining a change in the identifier data; and
in response to determining the change, updating the access control data structure based on the change.

27. The system of claim 16, wherein the operations further comprise:
facilitating a transmission of the access control data structure to the femtocell device.

28. The system of claim 16, wherein the access field indication data is first access field indication data and the operations further comprise:
configuring a set of tracking criteria associated with a transaction in a server of the macro network;
receiving data indicating that the transaction is determined to satisfy the set of tracking criteria; and
requesting second access field indication data associated with a communication device associated with the transaction, in response to determining that the transaction is associated with the femtocell device.

29. The system of claim 16, wherein the access field indication data further comprises billing data related to the mobile device.

30. A non-transitory computer-readable storage medium having instructions stored thereon that, in response to execution, cause a system comprising a processor to perform operations, comprising:
receiving access field indication data, comprising identifier data indicative of an identifier assigned to a mobile device;
receiving information relating to the mobile device from a subscriber data store within a macro network;
based on the information, determining that the identifier is not an active identifier; and in response to the determining, prohibiting addition of the identifier data to an access control data structure relating to a femtocell device associated with the mobile device, wherein the access control data structure is employed to control access to the femtocell device.

31. The non-transitory computer-readable storage medium of claim 30, wherein the identifier comprises a telephone number associated with the mobile device.

32. The non-transitory computer-readable storage medium of claim 30, wherein the operations further comprise:
receiving active identifier data indicative of the active identifier associated with the mobile device; and
updating the access control data structure with the active identifier data.

* * * * *